US 12,097,003 B2

(12) United States Patent
Sexson et al.

(10) Patent No.: US 12,097,003 B2
(45) Date of Patent: Sep. 24, 2024

(54) SYSTEM AND METHOD FOR INTERACTION AND DEFINITION OF TOOL PATHWAYS FOR A ROBOTIC CUTTING TOOL

(71) Applicants: ICAHN SCHOOL OF MEDICINE AT MOUNT SINAI, New York, NY (US); MONOGRAM ORTHOPAEDICS INC., Austin, TX (US)

(72) Inventors: Benjamin Sexson, Laguna Hills, CA (US); Douglas B. Unis, Brooklyn, NY (US); Matthew Dicicco, Brooklyn, NY (US); Brian Jin, New York, NY (US)

(73) Assignees: ICAHN SCHOOL OF MEDICINE AT MOUNT SINAI, New York, NY (US); MONOGRAM ORTHOPAEDICS INC., Austin, TX (US)

(*) Notice: Subject to any disclaimer, the term of this patent is extended or adjusted under 35 U.S.C. 154(b) by 217 days.

(21) Appl. No.: 17/455,822

(22) Filed: Nov. 19, 2021

(65) Prior Publication Data
US 2022/0071720 A1 Mar. 10, 2022

Related U.S. Application Data

(63) Continuation of application No. PCT/US2020/033810, filed on May 20, 2020.
(Continued)

(51) Int. Cl.
*A61B 34/37* (2016.01)
*A61B 34/00* (2016.01)
(Continued)

(52) U.S. Cl.
CPC ............ *A61B 34/37* (2016.02); *A61B 34/10* (2016.02); *A61B 34/20* (2016.02); *A61B 34/25* (2016.02);
(Continued)

(58) Field of Classification Search
CPC ......... A61B 34/37; A61B 34/10; A61B 34/20; A61B 34/25; A61B 90/361;
(Continued)

(56) References Cited

U.S. PATENT DOCUMENTS

| 9,119,655 B2 | 9/2015 | Bowling et al. |
| 9,119,665 B2 | 9/2015 | Ahern et al. |

(Continued)

FOREIGN PATENT DOCUMENTS

| DE | 102013211698 A1 | 12/2014 |
| WO | 2020236937 A1 | 11/2020 |
| WO | 2020243631 A1 | 12/2020 |

OTHER PUBLICATIONS

Sexson et al., International Search Report and Written Opinion for PCT/US2020/033810 (published as WO 2020/236937), titled "A System and Method for Interaction and Definition of Tool Pathways for a Robotic Cutting Tool", 14 pages, dated Oct. 23, 2020.
(Continued)

*Primary Examiner* — Jaime Figueroa
*Assistant Examiner* — Mohamad O El Sayah
(74) *Attorney, Agent, or Firm* — Heslin Rothenberg Farley & Mesiti P.C.

(57) ABSTRACT

A surgical method includes, for example, positioning a patient relative to a robot, moving an end effector of the robot relative to a surgical site of a patient, defining a go-zone and a no-go-zone associated with the surgical site based on the moving the end effector of the robot relative to the patient, and effecting a surgical procedure at the surgical (Continued)

site of the patient with a tool attached to the end effector of the robot based on the defined go-zone and the defined no-go-zone, and wherein the effecting the surgical procedure maintains the tool in the defined go-zone and avoids contact with the defined no-go-zone.

32 Claims, 19 Drawing Sheets

Related U.S. Application Data

(60) Provisional application No. 62/850,050, filed on May 20, 2019.

(51) Int. Cl.
*A61B 34/10* (2016.01)
*A61B 34/20* (2016.01)
*A61B 90/00* (2016.01)

(52) U.S. Cl.
CPC ...... *A61B 90/361* (2016.02); *A61B 2034/105* (2016.02); *A61B 2034/107* (2016.02); *A61B 2034/2055* (2016.02); *A61B 2034/2068* (2016.02)

(58) Field of Classification Search
CPC ........ A61B 2034/105; A61B 2034/107; A61B 2034/2055; A61B 2034/2068
See application file for complete search history.

(56) References Cited

U.S. PATENT DOCUMENTS

| | | | |
|---|---|---|---|
| 9,439,556 B2 | 9/2016 | Pandya et al. | |
| 9,603,665 B2 | 3/2017 | Bowling et al. | |
| 9,788,903 B2 | 10/2017 | Kim et al. | |
| 10,512,509 B2 | 2/2019 | Bowling et al. | |
| 10,716,630 B2* | 7/2020 | Krebs | A61B 5/055 |
| 2004/0106916 A1* | 6/2004 | Quaid | A61B 34/71 606/1 |
| 2006/0184275 A1* | 8/2006 | Hosokawa | B25J 9/1666 700/245 |
| 2011/0270443 A1* | 11/2011 | Kamiya | G05B 19/401 901/46 |
| 2013/0331644 A1 | 12/2013 | Pandya et al. | |
| 2014/0107471 A1 | 4/2014 | Haider et al. | |
| 2014/0200621 A1 | 7/2014 | Malackowski et al. | |
| 2014/0275760 A1 | 9/2014 | Lee et al. | |
| 2014/0316434 A1 | 10/2014 | Simaan et al. | |
| 2016/0058521 A1* | 3/2016 | Liang | G06T 19/00 703/11 |
| 2016/0113728 A1 | 4/2016 | Piron et al. | |
| 2016/0338782 A1* | 11/2016 | Bowling | A61B 90/39 |
| 2017/0056116 A1* | 3/2017 | Kostrzewski | G16H 40/63 |
| 2017/0071692 A1 | 3/2017 | Taylor et al. | |
| 2017/0258526 A1 | 9/2017 | Lang | |
| 2017/0265943 A1 | 9/2017 | Sela et al. | |
| 2017/0312031 A1 | 11/2017 | Amanatullah et al. | |
| 2017/0333137 A1 | 11/2017 | Roessler | |
| 2018/0000546 A1 | 1/2018 | Crawford et al. | |
| 2018/0297206 A1 | 10/2018 | Larkin et al. | |
| 2019/0142518 A1* | 5/2019 | Viscardi | A61B 34/74 606/130 |
| 2019/0142520 A1* | 5/2019 | VanDyken | G09B 23/30 606/1 |
| 2019/0314097 A1 | 10/2019 | Diolaiti | |
| 2019/0365481 A1 | 12/2019 | Otto et al. | |
| 2021/0137634 A1 | 5/2021 | Lang | |
| 2022/0079687 A1 | 3/2022 | Sexson et al. | |
| 2022/0125526 A1 | 4/2022 | Wald et al. | |

OTHER PUBLICATIONS

Sexson et al., International Search Report and Written Opinion for PCT/US2020/035408 (published as WO 2020/243631), titled "Robot Mounted Camera Registration and Tracking System for Orthopedic and Neurological Surgery", 8 pages, dated Jul. 30, 2020.

Wang et al., "Robot-assisted Occlusion Avoidance for Surgical Instrument Optical Tracking System", Proceeding of the 2015 IEEE International Conference on Information and Automation, 6 pages, Aug. 2015.

International Preliminary Report on Patentability for International Application No. PCT/US2020/033810, dated Nov. 16, 2021, 10 pages, International Bureau of WIPO.

Sexson et al., U.S. Appl. No. 17/456,989, "Robot Mounted Camera Registration and Tracking System for Orthopedic and Neurological Surgery", 76 pages, filed Nov. 30, 2021.

Partial Supplementary European Search Report for European Application No. 20809508.3 dated Jun. 15, 2023, 13 pages.

Partial Supplementary European Search Report for European Application No. 20813577.2 dated Jun. 27, 2023, 18 pages.

Australian Patent Office, First Examination Report dated Jan. 17, 2022, 5 pages.

DE-102013211698-A1 English Translation, 14 pages (Year:2014).

* cited by examiner

700 ⟶

```
┌─────────────────────────────────────────────────┐
│   POSITIONING A PATIENT RELATIVE TO A ROBOT     │── 710
└─────────────────────────────────────────────────┘
                        │
┌─────────────────────────────────────────────────┐
│ MOVING AN END EFFECTOR OF THE ROBOT RELATIVE TO │── 720
│         A SURGICAL SITE OF A PATIENT            │
└─────────────────────────────────────────────────┘
                        │
┌─────────────────────────────────────────────────┐
│ DEFINING A GO-ZONE AND A NO-GO-ZONE ASSOCIATED  │
│  WITH THE SURGICAL SITE BASED ON THE MOVING THE │── 730
│   END EFFECTOR OF THE ROBOT RELATIVE TO THE     │
│                    PATIENT                      │
└─────────────────────────────────────────────────┘
                        │
┌─────────────────────────────────────────────────┐
│  EFFECTING A SURGICAL PROCEDURE AT THE SURGICAL │
│   SITE OF THE PATIENT WITH A TOOL ATTACHED TO   │
│   THE END EFFECTOR OF THE ROBOT BASED ON THE    │
│ DEFINED GO-ZONE AND THE DEFINED NO-GO-ZONE, AND │── 740
│ WHEREIN THE EFFECTING THE SURGICAL PROCEDURE    │
│  MAINTAINS THE TOOL IN THE DEFINED GO-ZONE AND  │
│    AVOIDS CONTACT WITH THE DEFINED NO-GO-ZONE   │
└─────────────────────────────────────────────────┘
```

FIG. 15

SYSTEM AND METHOD FOR INTERACTION AND DEFINITION OF TOOL PATHWAYS FOR A ROBOTIC CUTTING TOOL

CROSS REFERENCE TO RELATED APPLICATIONS

This application is a continuation of International Patent Application No. PCT/US2020/033810, filed on May 20, 2020, entitled "A System And Method For Interaction And Definition Of Tool Pathways For A Robotic Cutting Tool" and published under the PCT Articles in English as WO 2020/236937 on Nov. 26, 2020, which International Patent application claims priority to U.S. Provisional Patent Application No. 62/850,050, filed May 20, 2019, entitled "A System And Method For Interaction And Definition Of Tool Pathways For A Robotic Cutting Tool", which applications are hereby incorporated herein by reference in its entirety.

TECHNICAL FIELD

The present disclosure generally relates to systems and methods used for robotic cutting tools used in surgery, and more specifically, orthopedic and neurological surgery, in accordance with such systems and methods.

BACKGROUND

The most commonly used method for moving industrial robots for teaching and interaction purposes is known as "jogging." Collaborative teaching methods are now being used on modern robots. The difficulties with jogging are that it is a slow and cumbersome process that makes it impractical for interactive use in time-sensitive surgical procedures. Collaborative robots have sensor and programming limitations which make use in the operating theater cumbersome.

In the field of orthopedic and/or neurological surgery, there are two commonly used robots and both are programmed prior to the surgery procedure. The MAKO robot is guided by the surgeon to the cutting area however a preprogrammed haptic boundary is used to prevent cutting into soft tissue. Issues arise when the cut nears the defined boundary, as the robot may be prevented from moving into ideal orientation for the appropriate cut. Additional challenges exist and changes to the boundary during surgery are minimal. The TSolution One robot is another example of a robot having to be programmed before the surgery and then functioning automatically to complete the surgical cut involved. This process results in tissue being resected regardless of any obstacles in its path or whether the cutting path is correct.

SUMMARY

Shortcomings of the prior art are overcome and additional advantages are provided through the provision, in one embodiment, of a surgical method, which includes for example, positioning a patient relative to a robot, moving an end effector of the robot relative to a surgical site of a patient, defining a go-zone and a no-go-zone associated with the surgical site based on the moving the end effector of the robot relative to the patient, and effecting a surgical procedure at the surgical site of the patient with a tool attached to the end effector of the robot based on the defined go-zone and the defined no-go-zone and wherein the effecting the surgical procedure maintains the tool in the defined go-zone and avoids contact with the defined no-go-zone.

In another embodiment, a surgical method may include, for example, positioning a patient relative to a robot, moving an end effector of the robot relative to a surgical site of a patient, defining a go-zone and a no-go-zone around the surgical site based on the moving the end effector of the robot relative to the patient, registering a bone of the patient at the surgical site to the robot, and effecting a resection or excavation of the bone of the patient at the surgical site with a tool attached to the end effector of the robot based on the defined go-zone, the defined no-go-zone, and the registered bone, and wherein the effecting the surgical procedure maintains the tool in the defined go-zone and avoids the defined no-go-zone.

In another embodiment, a surgical method may include, for example, positioning a patient relative to a robot, displaying on a display a representation of the surgical site of the patient, defining on the display a no-go-zone and go-zone associated with the representation of the surgical site, effecting a surgical procedure at the surgical site of the patient with a tool attached to the end effector of the robot based on the defined go-zone and the defined no-go-zone, and wherein the effecting the surgical procedure maintains the tool in the defined go-zone and avoids contact with the defined no-go-zone.

In another embodiment, a surgical method may include, for example, positioning a patient relative to a surgical robot, providing a secondary camera having for observing a surgical site of the patient, the secondary camera different from a camera for observing the surgical robot, tracking via the secondary camera an object adjacent to the surgical site, effecting a surgical procedure at the surgical site of the patient with a tool attached to an end effector of the surgical robot, and wherein the effecting the surgical procedure is based on the tracked object to avoid contact of the tool with the tracked object.

These, and other objects, features and advantages of the present disclosure will become apparent from the following detailed description of the various aspects of the present disclosure taken in conjunction with the accompanying drawings.

BRIEF DESCRIPTION OF THE DRAWINGS

The present disclosure will be understood more fully from the detailed description given hereinafter and from the accompanying drawings of certain embodiment of the present disclosure, which, however, should not be taken to limit the present disclosure, but are for explanation and understanding only.

FIG. 15 is a flowchart of a surgical method, according to an embodiment of the present disclosure;

DETAILED DESCRIPTION

Figure 1:
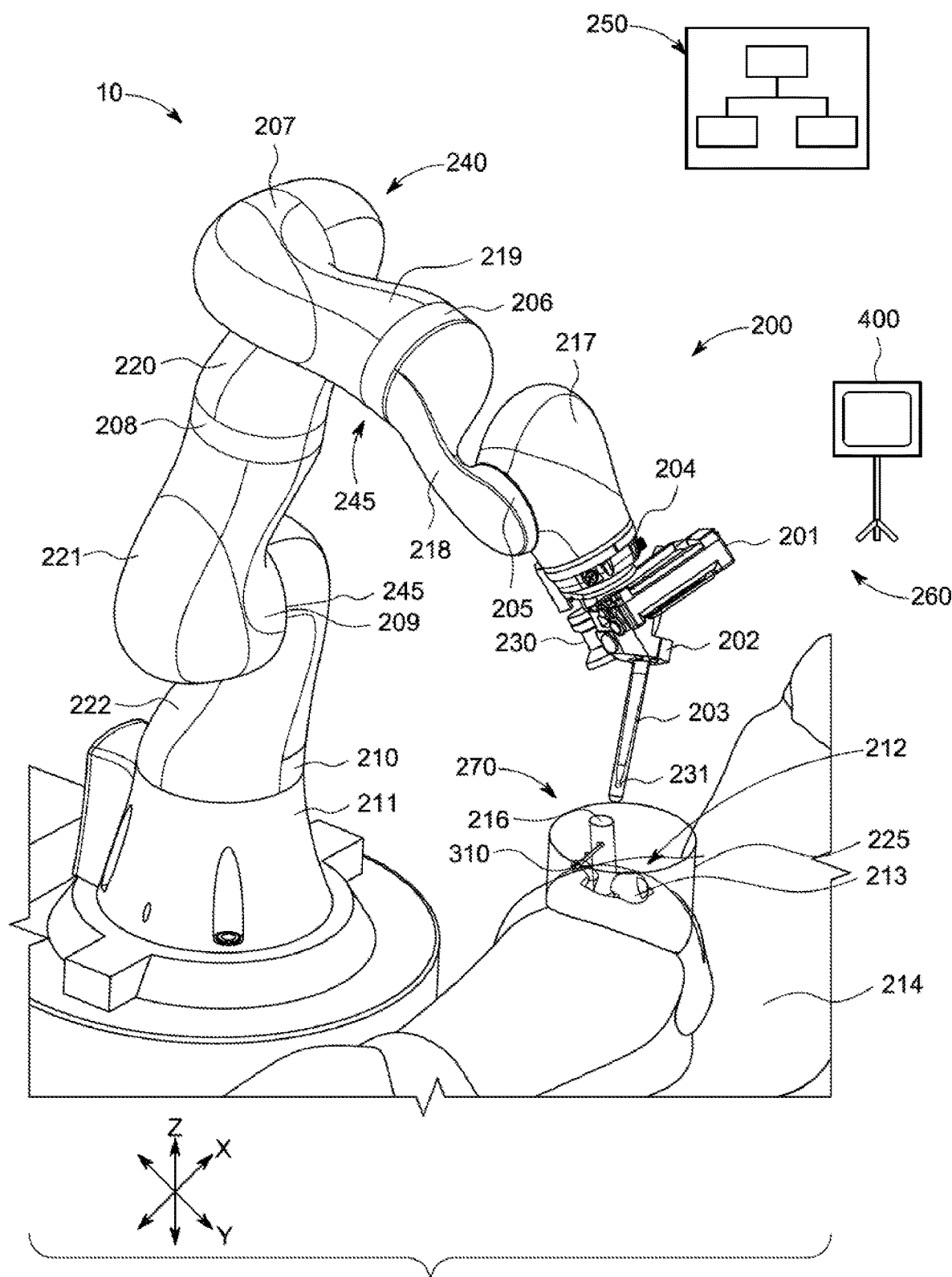
FIG. 1 is a perspective view of a surgical robotic system, according to an embodiment of the present disclosure.

The present disclosure will be discussed hereinafter in detail in terms of various exemplary embodiments with reference to the accompanying drawings. In the following detailed description, numerous specific details are set forth in order to provide a thorough understanding of the present disclosure. It will be obvious, however, to those skilled in the art that the present disclosure may be practiced without these specific details. In other instances, well-known structures are not shown in detail to avoid unnecessary obscuring of the present disclosure.

Thus, all the implementations described below are exemplary implementations provided to enable persons skilled in the art to make or use the embodiments of the present disclosure and are not intended to limit the scope of the disclosure, which is defined by the claims. As used herein, the word "exemplary" or "illustrative" means "serving as an example, instance, or illustration." Any implementation described herein as "exemplary" or "illustrative" is not necessarily to be construed as preferred or advantageous over other implementations.

Furthermore, there is no intention to be bound by any expressed or implied theory presented in the preceding technical field, background, summary or the following detailed description. It is to be understood that the specific devices and processes illustrated in the attached drawings, and described in the following specification, are simply exemplary embodiments. Hence, specific dimensions and other physical characteristics relating to the embodiments disclosed herein are not to be considered as limiting.

In this detailed description and the following claims, the words proximal, distal, anterior or plantar, posterior or dorsal, medial, lateral, superior and inferior are defined by their standard usage for indicating a particular part or portion of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure.

Similarly, positions or directions may be used herein with reference to anatomical structures or surfaces. For example, as the current instrumentation and methods are described herein with reference to use with the bones of the hip, the pelvis, and the femur may be used to describe the surfaces, positions, directions or orientations of the instrumentation and methods. Further, the instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the present disclosure. For example, the instrumentation and methods, and the aspects, components, features and the like thereof, described herein with respect to the right hip may be mirrored so that they likewise function with the left hip. Further, the instrumentation and methods, and the aspects, components, features and the like thereof, disclosed herein are described with respect to the hip for brevity purposes, but it should be understood that the instrumentation and methods may be used with other bones of the body having similar structures.

The systems, methods, and apparatus described are directed to inter-operatively defining, modifying, and removing a pre-defined zone or zones for a robotic cutting device used in orthopedic and/or neurological surgery due to differences between pre-operational surgical plan data defining a surgical protocol, and the actual surgical environment. In some embodiments, a surgical robot may be interactively taught and employed for accurately cutting pathways during a surgical procedure.

The following description references systems, methods, and apparatuses for cutting tools for orthopedic and/or neurological surgery involving a femur and the pelvic area.

However, those possessing an ordinary level of skill in the relevant art will appreciate that other extremities, joints, and parts of the musculoskeletal system are suitable for use with the foregoing systems, methods and apparatuses. Likewise, the various figures, steps, procedures and work-flows are presented only as an example and in no way limit the systems, methods or apparatuses described to performing their respective tasks or outcomes in different time-frames or orders. The teachings of the present disclosure may be applied to any orthopedic and/or neurological surgery such as on the shoulder, spine, elbow, and knee, and may be implemented in other treatments sites that have similar anatomical considerations.

Referring to FIG. 1, a surgical robotic system 10 may include a surgical robot 200, a control unit 250, and a user interface 260 (UI), according to an embodiment of the present disclosure. The control unit 250 may include at least one processing circuit, at least one input/output device, at least one storage device or memory having at least one database as further described below. The control unit 250 may have a control algorithm or programming code for controlling, for example, joint angle. The control algorithm or programming code may be a default control algorithm or include inputs from, for example, a Fast Robotic Interface.

The surgical robot 200 may include a base 211 and a plurality of body parts 240 and a plurality of joints 245. The plurality of joints 245 may include, for example, a flange 204, a first joint 205, a second joint 206, a third joint 207, a fourth joint 208, a fifth joint 209, and a sixth joint 210. The plurality of body parts 240 may include, for example, a first body part 217, a second body part 218, a third body part 219, a fourth body part 220, a fifth body part 221, and a sixth body part 222.

The sixth joint 210 may be connected to the base 211 and to the sixth body part 222, with, for example, sixth body part being rotatably movable at the sixth joint 210 about the base 211. The fifth joint 209 may be connected to the sixth body part 222 and to the fifth body part 221, with, for example, the fifth body part 221 and the sixth body part 222 being rotatably movable relative to each other about the fifth joint 209. The fourth joint 208 may be connected to the fifth body part 221 and the fourth body part 220, with, for example, the fifth body part 221 and the fourth body part 220 being rotatably movable relative to each other about the fourth joint 208. The third joint 207 may be connected to the fourth body part 220 and the third body part 219, with, for example, the fourth body part 220 and the third body part 219 being rotatably movable relative to each other about the third joint 207. The second joint 206 may be connected to the third body part 219 and the second body part 218, with, for example, the third body part 219 and the second body part 218 being rotatably movable relative to each other about the second joint 206. The first joint 205 may be connected to the second body part 218 and the first body part 217, with, for example, the second body part 218 and the first body part 217 being rotatably movable relative to each other about the first joint 205.

The base 211 may be fixed to, for example, a cart or the ground, such that the base 211 may provide a fixed frame of reference for defining the position, orientation, and motion of the plurality of joints 245 and the plurality of body parts 240 relative to the base 211. The base 211 may be used to define a frame of reference, such as, for example, a set of three-dimensional axes (e.g., x, y, z), which may be used to define positions, orientations, and motions of the surgical robot 200 and of objects relative to the surgical robot 200. A frame of reference defined relative to the base 211 may also be known as a world frame, a base, a base frame, a frame, or a tool frame. If the position and orientation of an object may be defined or calculated in relation to a position relative to the world frame, the object becomes defined in the same frame of reference as the surgical robot 200, and the surgical robot 200 may calculate the position and orientation of the object. As such, the surgical robot 200 may programmably interact with the defined objects, positions, and/or orientations.

Referring further to FIG. 1, since the position, orientation, and motion of the plurality of joints 245 and the plurality of body parts 240 relative to the base 211 may be defined, and the flange 204 may be connected to the first body part 217 and to the end effector 202, the position, and orientation of the flange 204 and the end effector 202 may be calculated. The first body part 217 and the end effector 202 may be rotatably movable relative to each other about the flange 204, and thus their motion may also be determined. The flange 204 may also be referred to as, for example, a mounting flange, surgical robot arm flange, or output flange, and may represent a mounting member at the proximal tip the first body part 217 of the surgical robot 200.

Connected to the end effector 202 may be a tool 203, a control handle 201, and a camera 230, according to an embodiment of the present disclosure. By virtue of connection with the end effector 202, the position, orientation, and motion of the tool 203, the control handle 201, and the camera 230 may be determined, if the position, orientation, and motion of the end effector 202 may be determined. If the position, orientation, and motion of the tool 203 may be determined, the position, orientation, and motion of a tool tip 231 may also be determined. It is understood that the tool 203 is configured for cutting bone, however the tool 203 may be replaceable with non-cutting implements that may function as, for example, a marking device or a viewing device.

The position, orientation, and motion of each of the plurality of joints 245 and each of the plurality of body parts 240 that are components of the surgical robot 200, may be calculated and determined relative to the base 211. The position and orientation of objects external to the surgical robot 200, such as a marker 215 (best shown in FIG. 2), may be determined if the object is within the field of view of the camera 230. The object's position and orientation may be determined relative to the camera 230. The position and orientation of the camera 230 may be defined because the position and orientation of the components of the surgical robot 200 may be determined. If the position, orientation, and motion of each of the plurality of joints 245 and each of the plurality of body parts 240 are determined relative to the base 211, then the position and orientation of an external object may be calculated for surgical robot interaction. Similarly, the definition of an external position and orientation relative to the base 211, may make that position and orientation defined relative to the surgical robot 200 such that the surgical robot 200 may interact with the defined external position.

Figure 2:
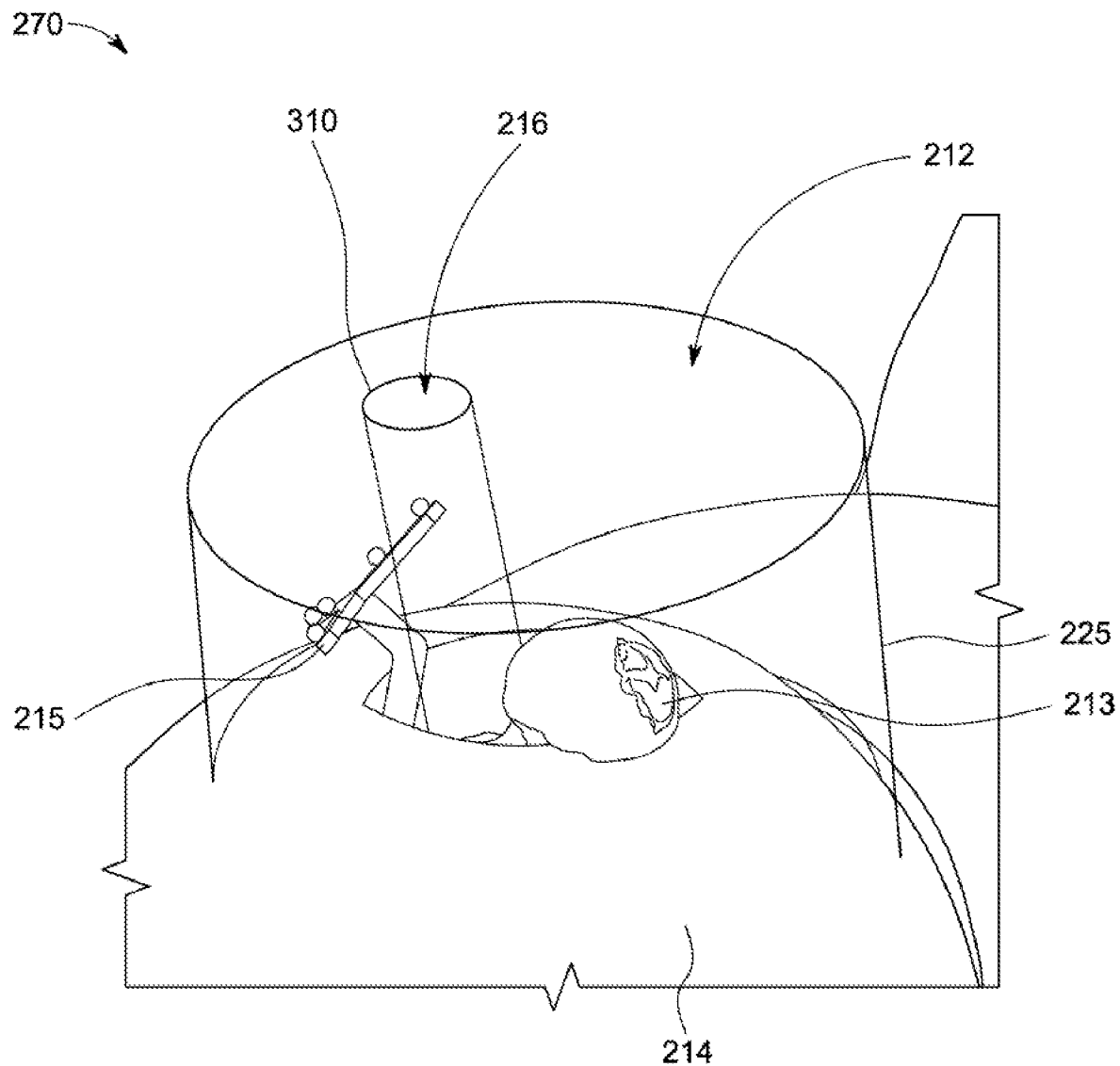
FIG. 2 is an enlarged perspective view of the surgical site and illustrated boundary zones of FIG. 1, according to an embodiment of the present disclosure.

With reference to FIG. 2, a surgical site 270 of a patient 214 is show along with an illustration of a defined cutting zone or go-zone 216 and a no-go-zone 212, according to an embodiment of the present disclosure. The marker 215 is shown inserted into the patient 214 in a surgical site 270 near a femur 213, shown protruding from the surgical site 270. The marker 215 may also be referred to as a position marker or reference marker. The surgical site 270 may be understood to be the area where surgery is being performed on the patient 214. The marker 215 may be used, for example, to define positions and orientations on the femur 213 or on the patient 214, relative to the marker 215, such that if the position and orientation of the marker 215 is definable relative to the base 211 (FIG. 1), then the positions and orientations defined on the femur 213 or on the patient 214 may be calculable relative to the base 211. If, for example, the positions and orientations on the femur 213 or the patient 214 are defined relative to the base 211 (FIG. 1), then the surgical robot 200 may act on positions and orientations on the femur 213 or the patient 214.

In alternate embodiments, the position of objects and locations may be mapped relative to a bone, e.g., the femur 213, being operated on, rather than the world frame.

As used here, the expression "no-go-zone" may be interchangeably used with the expressions "unsafe zone" or "boundary constraint." The expression "go-zone" may be interchangeably used with the expression "safe zone" or "keep-out zone." The expression "default no-go-zone" may also be referred to as "default boundary constraint."

As shown in FIG. 1, a user interface (UI) 260 may include the control handle 201 and a visual display device 400 that can be used by a surgeon to interact with the surgical robot 200 and the control unit 250, according to an embodiment of the present disclosure.

With reference to FIGS. 3-9, in this illustrated embodiment, the UI 260 (FIG. 1) may include, for example, the control handle 201 (FIGS. 3-5) and a visual display screen 400 (FIGS. 6-9). Other embodiments may include, for example, a plurality of foot pedals, a keyboard and mouse, an augmented reality display, or other suitable input/output device. In still other embodiment, a control handle 201 (FIG. 3-5) may not be required such as where the end effector 202 is sized and configured to be easily gripped by a surgeon as described in greater detail below. The UI 260 (FIG. 1) provides an input and feedback system which may allow user inputs to the surgical robot 200 (FIG. 1) and control unit 250 (FIG. 1), and returns information from the surgical robot 200 (FIG. 1) and the control unit 250 (FIG. 1) to the user.

Figure 3:
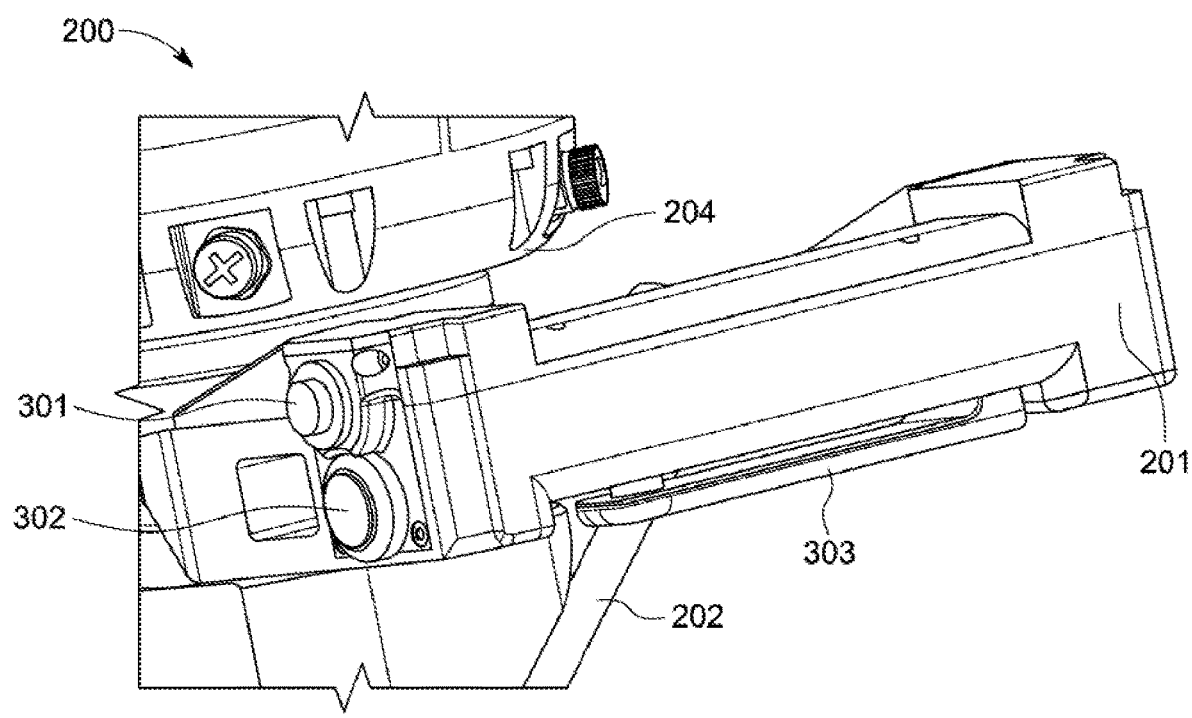
FIG. 3 is a perspective side view of the control handle of the surgical robotic system of FIG. 1, according to an embodiment of the present disclosure.
Figure 4:
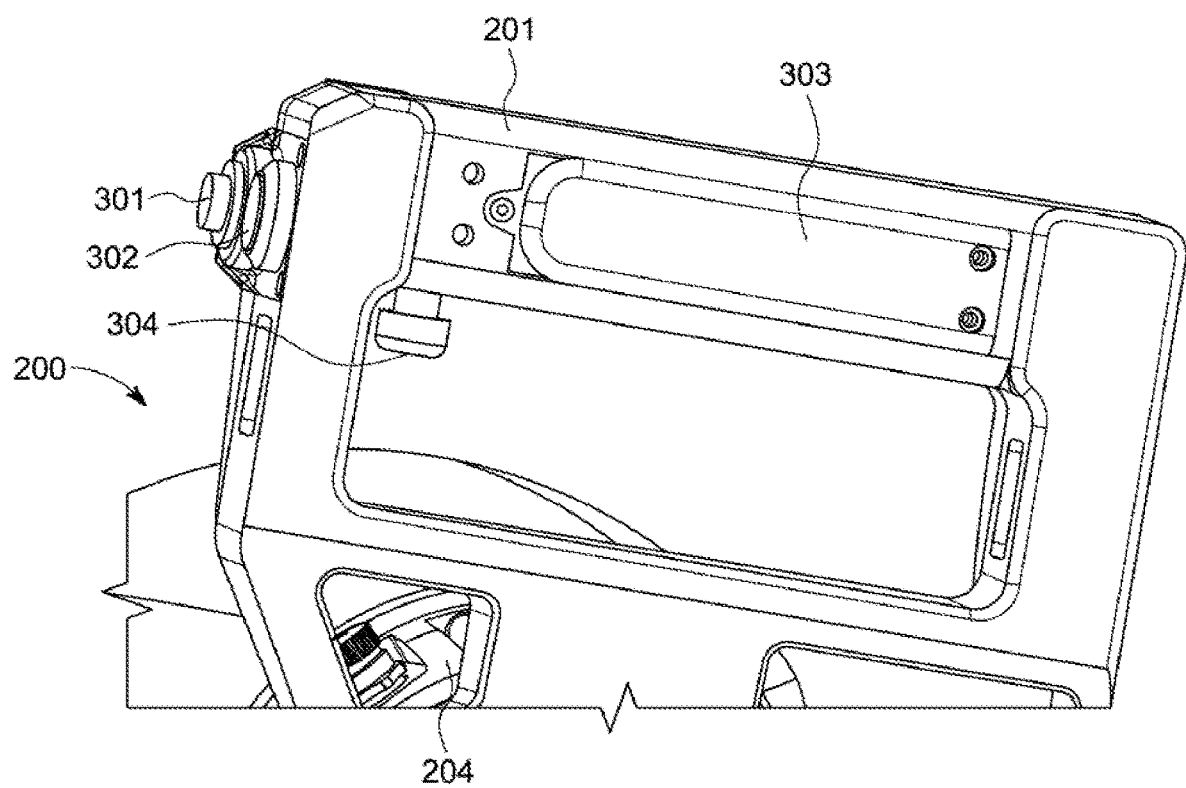
FIG. 4 is a perspective bottom view of the control handle of the surgical robotic system of FIG. 3, according to an embodiment of the present disclosure.
Figure 5:
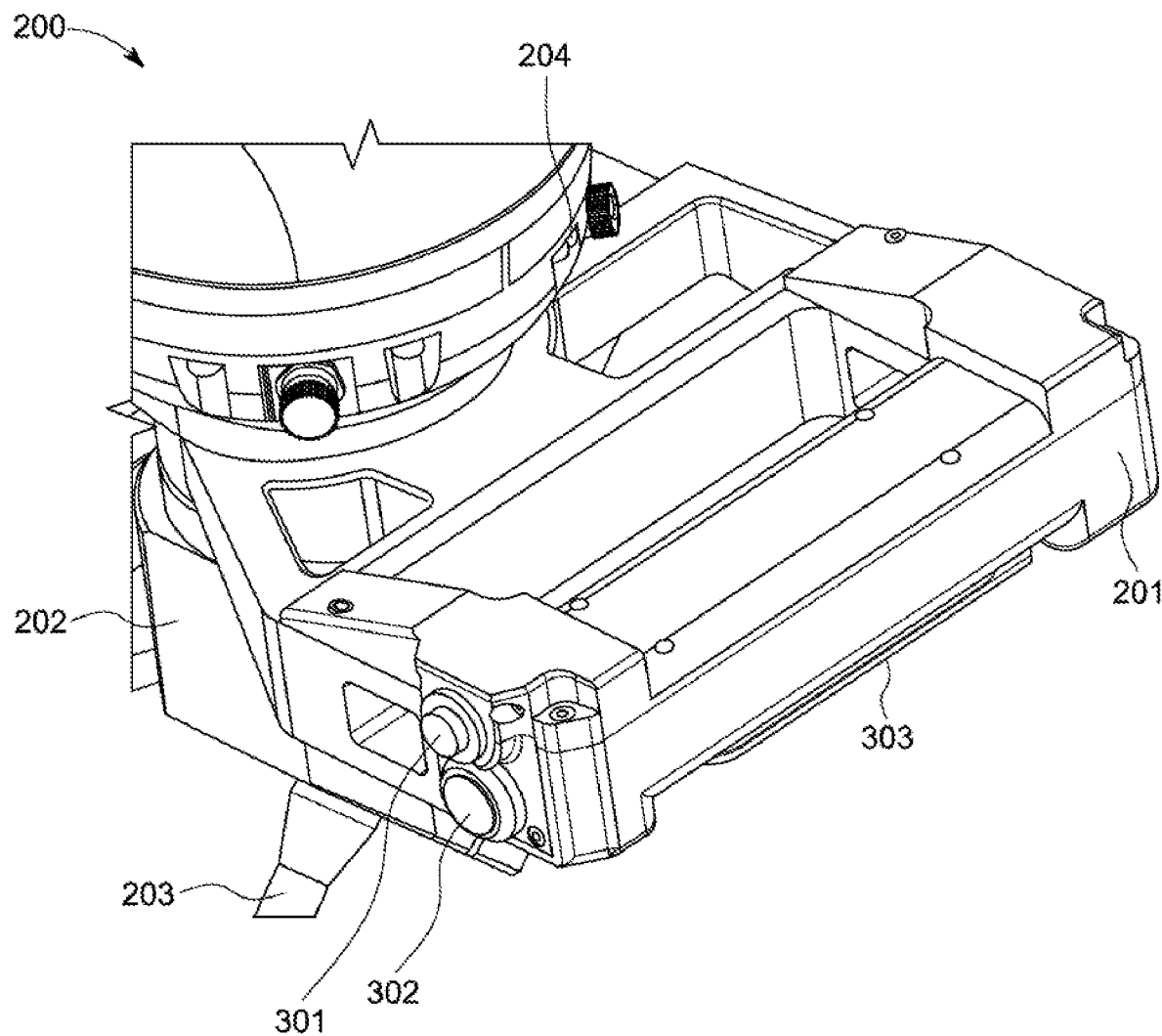
FIG. 5 is a perspective top view of the control handle of the surgical robotic system of FIG. 3, according to an embodiment of the present disclosure.

As shown in FIGS. 3-5, the control handle 201 may include a primary thumb button 301, a secondary thumb button 302, a trigger button 304, and a position switch 303, according to an embodiment of the present disclosure. The control handle 201 may be, for example, a single, horizontally mounted control handle, mounted to the flange 204, in a position close to the user. The control handle 201 may also include, for example, a generally small footprint so as to allow additional sensors to be mounted at the end effector 202 (FIG. 3), e.g., the camera 230 (FIG. 1) and to minimize viewing obstruction of the patient 214 (FIG. 1). The position switch 303 may be used for primary activation of functions that may be performed by the surgical robot 200. The position switch 303 may also act as a safety where the surgical robot motion and activity stops or is inhibited when the position switch 303 is released. An embodiment of the position switch 303 may be, for example, a three-position switch, requiring a nominal level of grasping force to activate functions, and over-gripping or under-gripping stops the functions. The position switch 303 may also trigger data collection functions, such as, for example, automatically collecting registration points or other location and position data collection.

The primary thumb button 301 may be used to initiate zero-g mode and enable free robot movement in zero-g mode. The primary thumb button 301 may be constructed to stop zero-g mode upon release. Pressing the primary thumb button 301 may initiate zero-g mode, but the position switch 303 may also need to be simultaneously held to allow the surgical robot 200 to move.

The secondary thumb button 302 is shown as a single button, but there may be more than one secondary thumb button 302, which may activate other functions and feedback. The standard zero-g like behavior is normally a fully unconstrained motion, with system translation and rotation being without restriction. To aid in positioning, the secondary thumb button 302 may be used, for example, to select or toggle between different lockout modes, such as: an unconstrained motion, an orientation lock, a position lock, a planar lock, or a tool-axis lock. These different modes may provide for direct interaction with and control of the surgical robot 200. With orientation lock applied, using the primary thumb button 301 may maintain the orientation of the system specified but allows for the system to translate freely. Position lock may provide a selection, for example, locking the end effector 202 (FIGS. 3 and 5) or the tool tip 231 (FIG. 1) position, while allowing the system to be rotated freely about the end effector 202 (FIGS. 3 and 5) or the tool tip 231 (FIG. 1). With planar lock engaged, the orientation of a cutting tool 203 (FIG. 4) may be locked for vertical motion, relative to its vertical position (i.e., up or down relative to the tool 203 (FIG. 4) position), but surgical robot 200 may be moved along a horizontal plane, relative to the current position of the tool 203 (FIG. 4), i.e., a plane defined by an X axis and a Y axis of the position of the tool 203 (FIG. 4)). With tool-axis lock, the orientation and position of the tool 203 (FIG. 4) remains fixed, except for translation and orientation along the tool's primary axis.

The combination of buttons and the control handle 201 provides a direct method to affect the control algorithms of the surgical robot 200. The interaction control handle 201 serves as a point of engagement with the surgical robot 200 where the user can operably position and/or hold the surgical robot 200, as well as providing control over the modes of operation of the surgical robot 200.

The trigger button 304 may be pressure sensitive and controls the speed of the surgical robot's 200 motion during cutting and along a cut path.

An alternate embodiment of the present disclosure may transfer some or all of the functions performed by the primary thumb button 301, the secondary thumb button 302, and the trigger button 304 to foot pedals. For example, control over zero-g mode may still be retained by the control handle 201 rather than through foot pedals, so as to prevent the surgical robot 200 from falling unguided.

With reference to FIGS. 6-9, as part of the interaction with the surgical robot 200 (FIG. 1), a visual display device 400 may be observed by a surgeon and/or used for additional user input and/or user feedback. The visual display device 400 may include but not be limited to a computer monitor, a touch screen computer monitor, or an augmented reality display, or other suitable visual display.

The visual display device 400 is operable to provide the user with perspective or three-dimensional representations of the various features and components corresponding to the various features and components at the actual surgical site 213 (FIG. 1). For example, the visual display device 400 may provide a representation of the surgical site 1270 along with representations of cutting zones and unsafe zones overlaid above the representation of the patient 1214 and/or over the representation of the surgical site 1270. Input to the visual display device 400, may be from at least one camera 230 (FIG. 1) mounted to the end effector 202 (FIG. 1) or through an assortment of sensors mounted to the end effector 202 (FIG. 1). A user may be able to interact with the information displayed on the visual display device through a keyboard and mouse, through a touch screen monitor, or through position and motion sensors in the augmented reality display.

Figure 6:
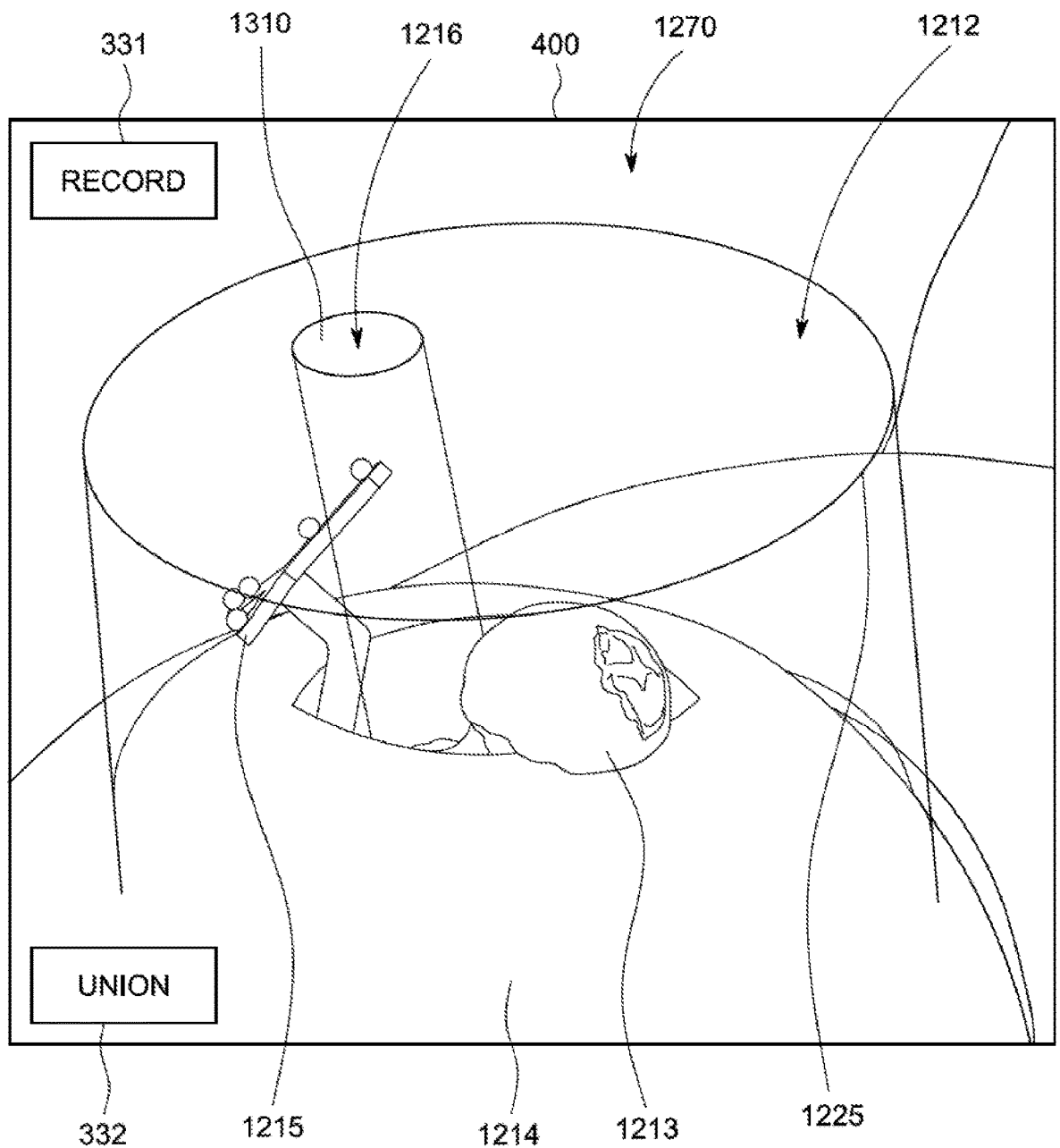
FIG. 6 is a view of a surgical planning display displaying representations of the surgical site and boundary zones of FIG. 1, according to an embodiment of the present disclosure.
Figure 7:
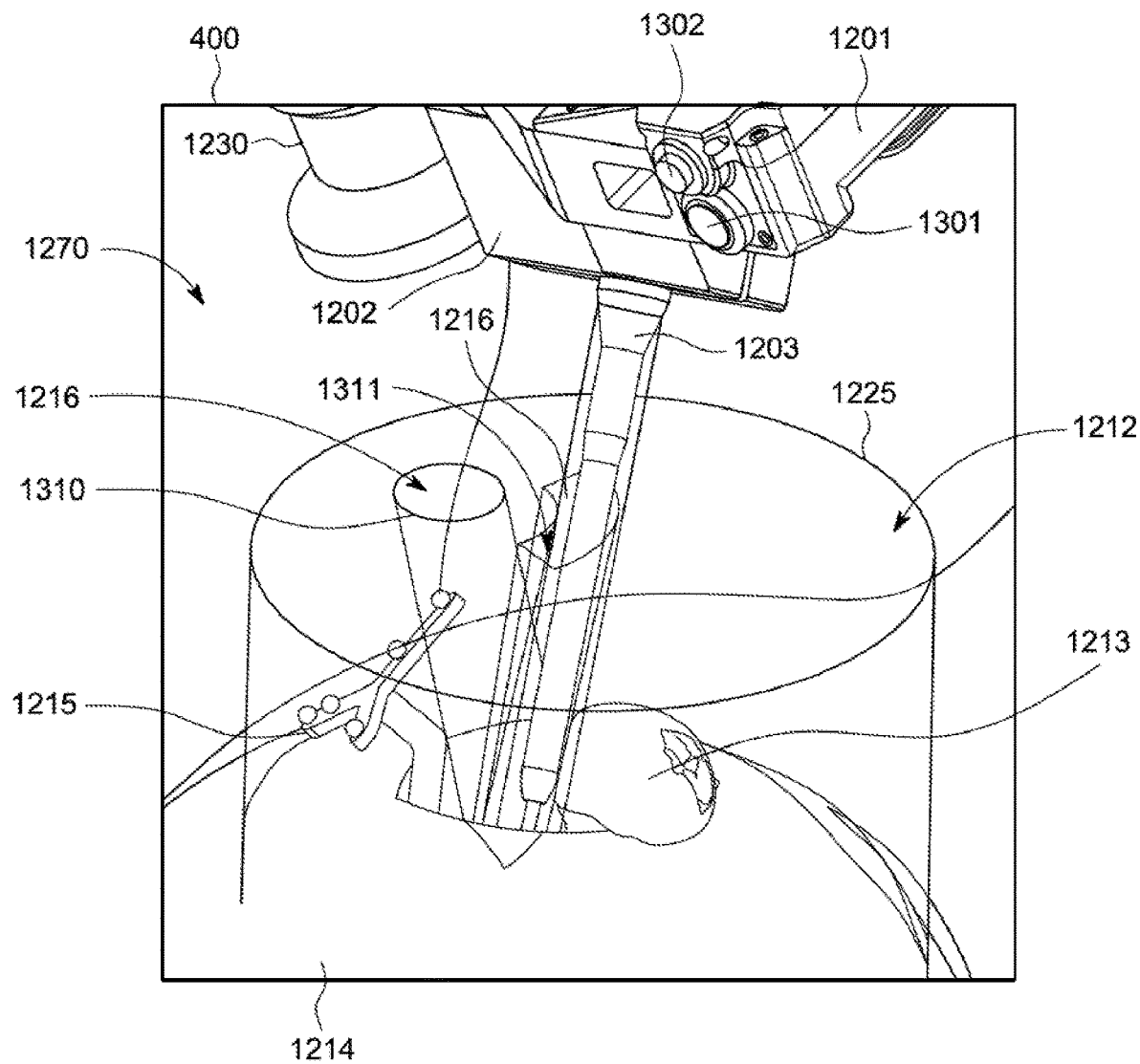
FIG. 7 is a view of the surgical planning display of FIG. 6 displaying representations of the surgical site, the boundary zones, and the end effector of the surgical robot, according to an embodiment of the present disclosure.

As shown in FIGS. 6 and 7, the visual display screen 400 may display, for example, the surgical site 1270, a representation of the default boundary 1225 depicting a representation of the no-go-zone 1212, and a representation of the default go-zone boundary 1310 depicting a representation of the go-zone 1216 disposed above the patient 1214 and the surgical site 1270. Within the surgical site 1270, a representation of the marker 1215 and a representation of the femur 1213 may be visible.

Figure 8:
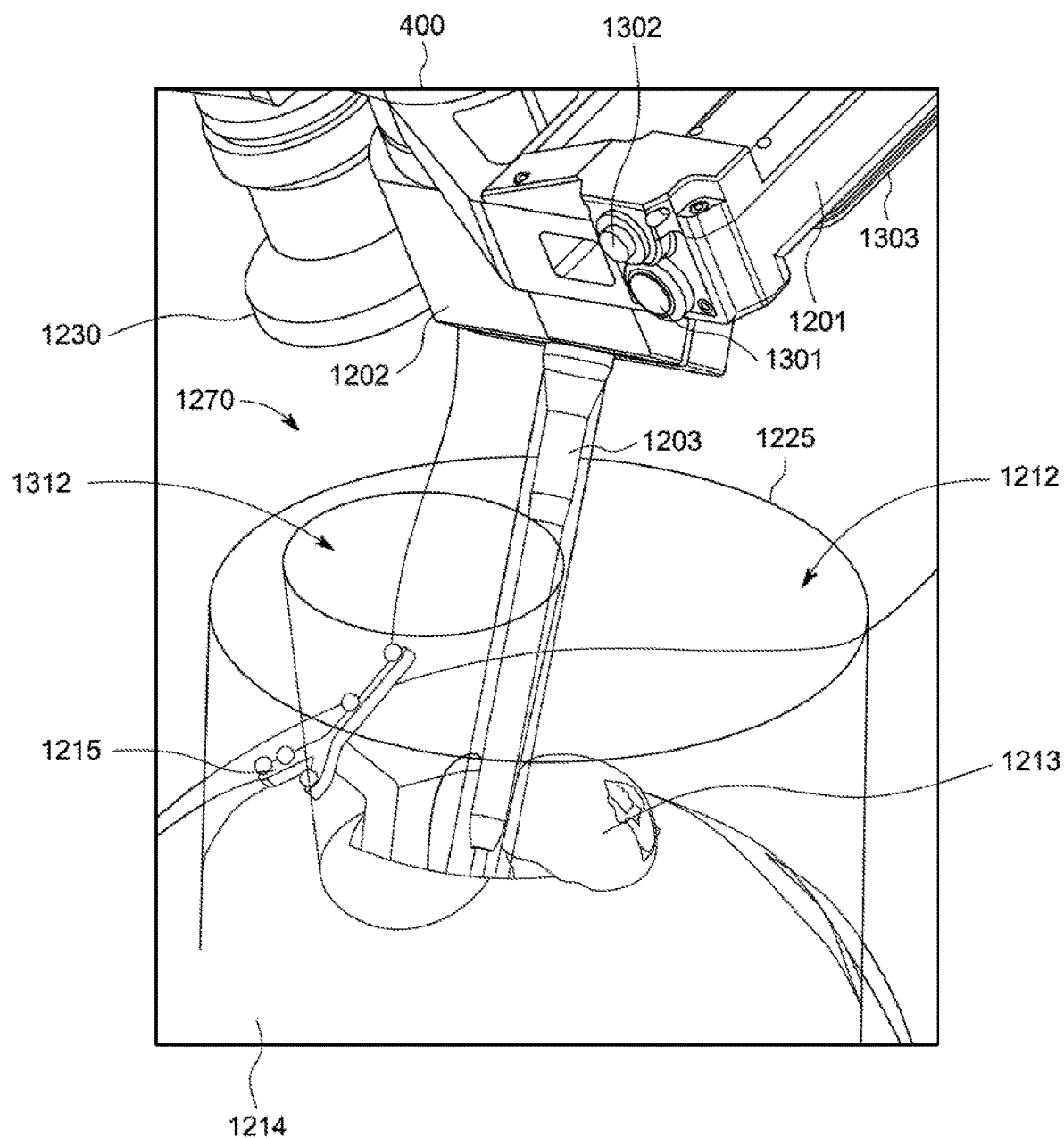
FIG. 8 is a view of the surgical planning display of FIG. 6 displaying representations of the surgical site, a modified boundary zone, and the end effector of the surgical robot, according to an embodiment of the present disclosure.
Figure 9:
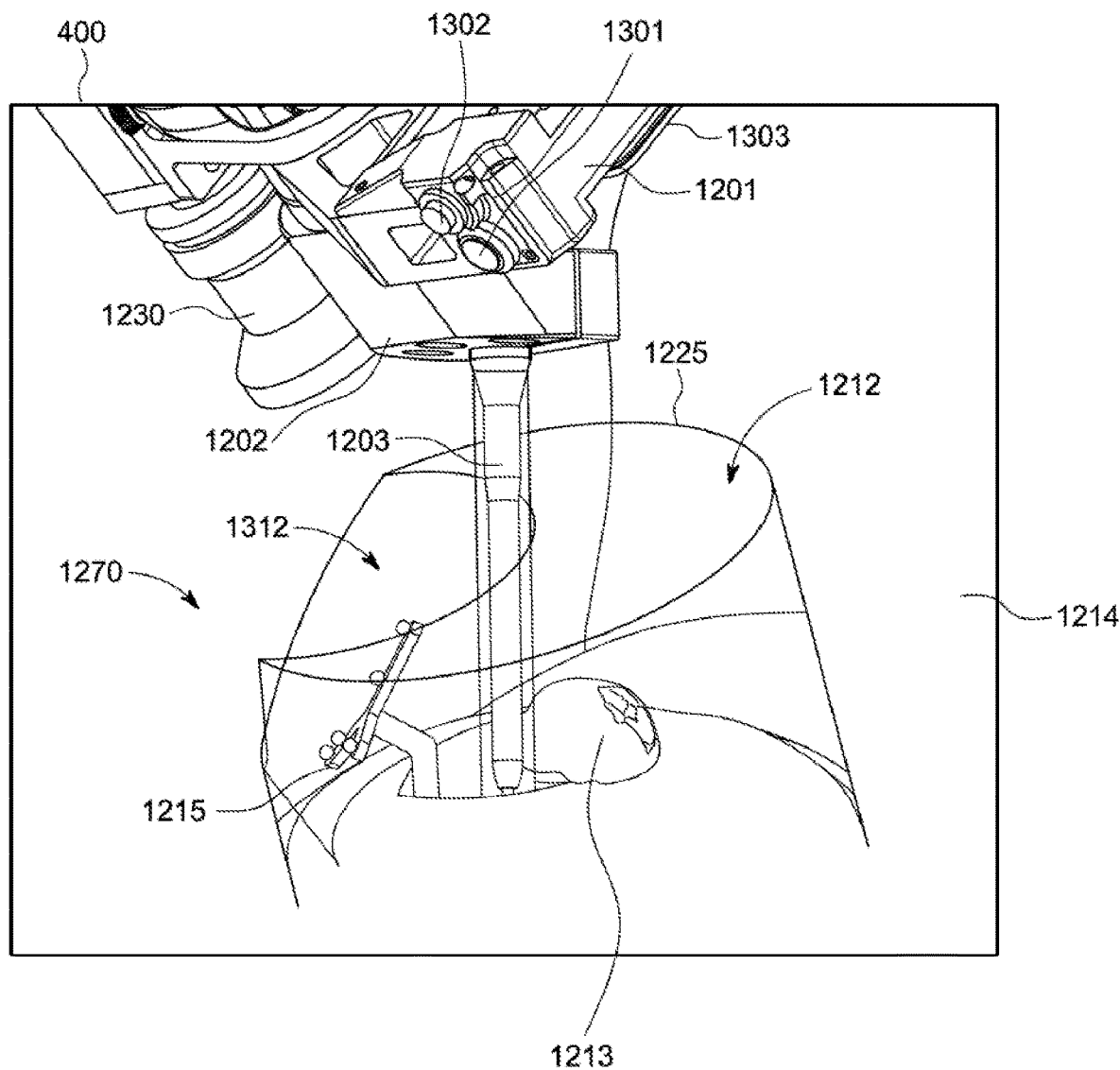
FIG. 9 is a view of the surgical planning display of FIG. 6 displaying representations of the surgical site, a completed expansion of the boundary zones, and the end effector of the surgical robot, according to an embodiment of the present disclosure.

Referring to FIGS. 7-9, the visual display screen 400 is shown displaying, for example, a representation of the camera 1230, a representation of the control handle 1201, a representation of the primary thumb button 1301, a representation of the secondary thumb button 1302, the representation of the end effector 1202, and a representation of the tool 1203. The tool 1203 is shown being used to create a representation of a second go-zone 1311 (FIG. 7) near the default go-zone 1310, the position marker 1215, and the femur 1122, with a cutting zone 1220, and a no-go-zone 221 defined. Within the surgical site 1270, the marker 1215 and a representation of the femur 1213 are visible and the cutting tool 1203 may also be seen within the surgical site 1270. The second go-zone 1311 may intersect the default go-zone 1310 and the cutting tool 1203 may be moved, for example in a conical motion using a position lock to create an enlarged go-zone 1312 (FIGS. 8 and 9). In other embodiments, the tool may be moved to define a portion of a cylinder, a portion of a cone, a cylinder, or a cone. The cutting tool may be Once multiple go-zones are created, a union of go-zones may be created resulting in, for example, a final go-zone. In other embodiment, the display may illustrate the surgical site without the surgical robot, and a user may define the no-go zone and go-zone by touching the display to create the go-zone and the no-go-zone.

Figure 10:
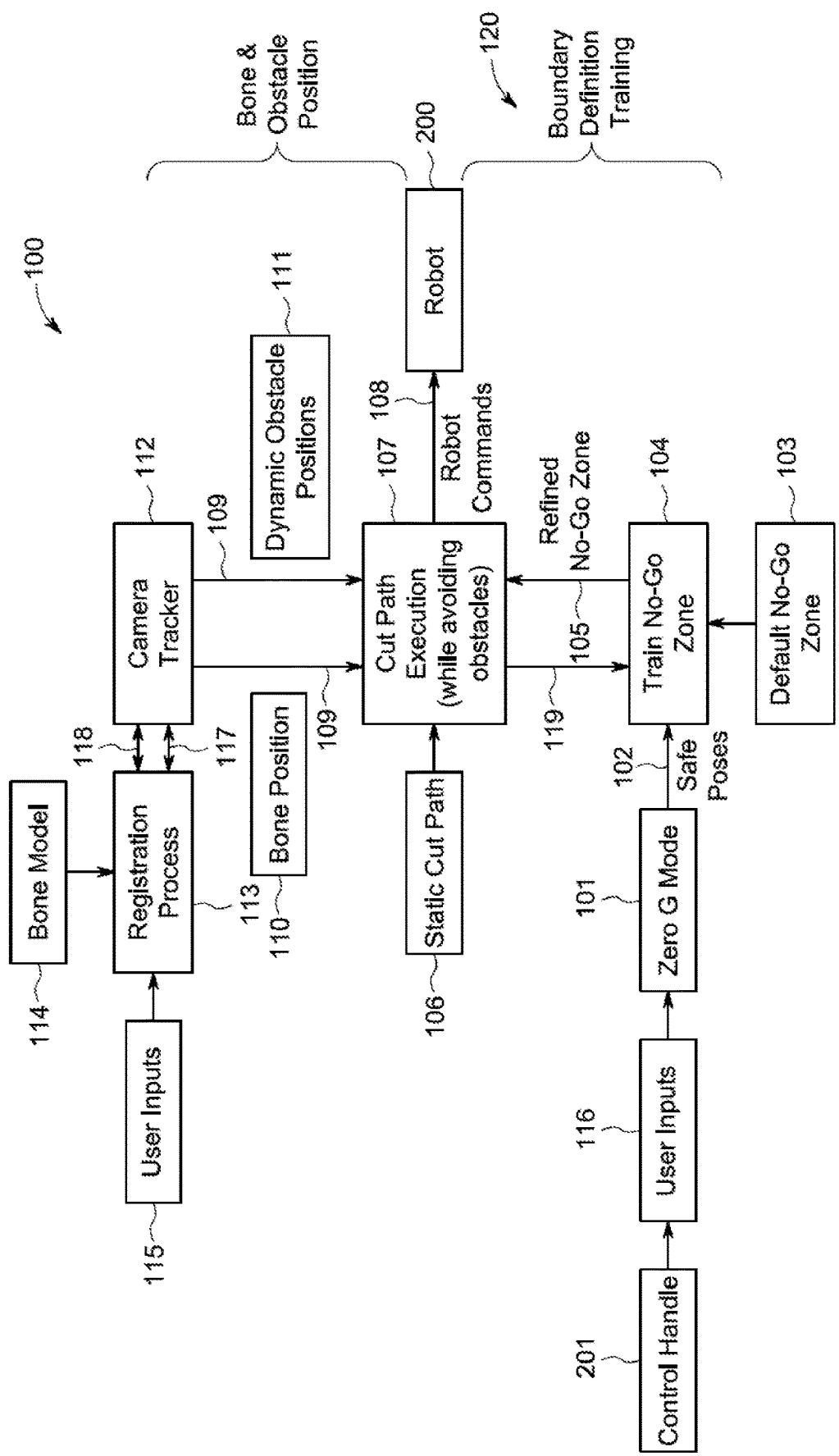
FIG. 10 is an interaction block diagram depicting a method for creating cut path execution commands and sending cut path execution commands to a surgical robot, according to an embodiment of the present disclosure.

FIG. 10 illustrates a block diagram of a method for creating cut path execution commands and sending cut path execution commands to the surgical robot 200. In describing the method of FIG. 10, reference may be made to corresponding components of the surgical robotic system (FIG. 1). FIG. 10 is divided into upper and lower blocks, with the upper and lower blocks providing input to a cut path execution block 107 and the surgical robot 200. The inputs to the cut path execution block 107 may collectively be known as surgical plan data. The upper blocks concern the definition of a bone, such as the femur 213 (FIG. 1), and obstacle positions. The upper blocks describe a method to determine the surgical robot's position relative to the surgical site and to map the surgical site by determining the bone position and the dynamic position of obstacles. A bone model 114 and user registration inputs 115 are provided in a registration process 113. This model may be provided via, for example, a computerized tomography scan segmentation. The registration process 113 may include, for example, using the bone model 114 to define an initial bone position and receiving user inputs 115 to define actual bone position in relation to a frame of reference and updating the bone model 114. Actual bone positions may, for example, be defined in relation to a marker 215 (i.e., the frame of reference). The registration process 113 may further include, for example, a processor performing a transform chaining operation to transform positions defined on the femur 213 relative to marker 215, to positions on the femur 213 (FIG. 1) relative to a frame of reference defined by the base 211 (FIG. 1). Position data of the surgical robot 200 and the relative position of objects or locations may be stored or updated in a database or a storage medium. The registration process 113 may provide registration process data 117 (e.g., updated bone model data) to a camera tracker 112. The camera tracker 112 may further update the bone model 114 by, for example, transforming the frame of reference of the bone model to a frame of reference relative to the surgical robot 200 and further sending camera tracker data 118 to the registration process 113 for further bone model refinement. Camera tracker data 118 may include, for example, the position of marker 215 (FIG. 1) relative to the base 211 (FIG. 1), and the relative positions on the femur 213 (FIG. 1) or may include just the positions on the femur 213 (FIG. 1) relative to the marker 215 (FIG. 1), with just marker location being determined. Camera tracker data 118 input from the camera tracker 112 and, for example, updates to the bone model 114 using updated bone model data 117 and camera tracker data 118. The exchange of camera tracker data 118 and registration process data 117 between the registration process 113 and the camera tracker 112, provides a final bone model 109 by, for example, registering the user inputs 115 of actual bone position on the bone model 114 in relation to a frame of reference relative to the surgical robot 200. The final bone model 109 may include, for example, the bone position 110 and the dynamic obstacle position 111 being sent to the cut path execution processing block 107. The camera tracker 112 may wait for the registration process 113 to complete before sending the final bone model 109 to the cut path execution processing block 107, or the final bone model 109 may dynamically update the cut path execution processing block 107.

With reference again to FIGS. 6-9, objects which have been registered and/or defined for the surgical robotic system 10 (FIG. 1) and/or the surgical robot 200 may be represented and visualized on the visual display screen 400. The registration process 113 (FIG. 10) correlates a real time position of an object to a pre-operative model. Therefore, a patient's bones or the surgical robot 200 or surgical objects, such as, for example, a retractor and marker 215 (FIG. 1), may be represented and displayed. The visual display screen 400 may include representation of objects with known positions, and those representations of objects may be tracked. The visual display screen 400 may be used by the surgeon to interact through the surgical robotic system 10 (FIG. 1) and/or the surgical robot 200 with the surgical workspace. The display 400 may provide different perspectives on the surgical workspace, such as, for example, a zoom function or an orientation change function. The display 400 may receive input from not only the robot mounted camera 230 (FIG. 1) but also off-robot cameras which may be connected to the surgical robot 200 (FIG. 1).

With reference again to FIGS. 3-5, defining boundary conditions may be performed using multiple methods. A first method may include using the control handle 201 to manually move the surgical robot 200 into positions to define go-zones or no-go-zones or modify a boundary. A second method may include interacting with the visual display screen 400 (FIGS. 6-9) by using a mouse, stylus, or touchscreen to create or remove a boundary. A third method may include defining a boundary pre-operatively. The three methods may be used individually or in combination with each other. The term training may be used when referring to using the control handle 201 to move the surgical robot 200 to define boundary positions and such actions may be used in conjunction with recording the positions and orientation of the surgical robot 200.

The lower blocks of FIG. 10 describe a method for defining boundary conditions for input into the cut execution process 107 by boundary definition training 120 to the surgical robot 200. User training inputs 116 are provided by using the control handle 201 to place the surgical robot 200 into a zero-g mode 101 and defining safe poses 102, based on a model of default no-go-zones, in a process of training no-go-zones 104, and providing a refined no-go-zone 105 to the cut path execution process 107. The control handle 201 may provide multiple controls for multiple interaction commands for the surgical robot 200, including, for example, controls for modes of operation. The surgical robot 200 may have at least two interaction modes, for example, a move mode and a cutting mode. Move mode places the surgical robot into a zero-g state, allowing the surgical robot 200 to be manually moved. As used here, the expression "zero-g state" or "zero-g mode" may be used interchangeably with "move mode". Through the control handle 201, user inputs 116 place the surgical robot 200 into a mode of operation that includes zero-g mode 101. Zero-g mode may include the surgical robot 200 being manually moved into a desired position as the surgical robot 200 actively supports the weight of the plurality of joints 245 (FIG. 1) and plurality of body parts 240 (FIG. 1), without actively trying to maintain the position of the plurality of joints 245 (FIG. 1) and the plurality of body parts 240 (FIG. 1) position.

To train no-go-zones 104, the surgical robot 200 may be placed into move mode by pressing the primary thumb button 301 (FIGS. 3-5) to initiate zero-g mode, followed by pressing the position switch 303 (FIGS. 3-5) to allow movement of the surgical robot 200, and moving the surgical robot 200 to an initial position near a surgical site by pulling or pushing on the control handle 201. This position may be at or near the surgical site 270 (FIG. 1). After the registration process 113 has been performed, cut path execution data 119 may be provided to begin no-go-zone training 104. The cut path execution data 119 provided to no-go-zone training may be in the form of the bone position 110, dynamic obstacle positions 111, and a static cut path 106. Cut types include, for example, a neck cut, femoral milling or acetabular reaming. This information may be displayed as a computer simulation on visual display screen 400. Default no-go-zone data 103 may be provided for no-go-zone training 104. Default no-go-zone 103 data may be displayed, for example, as a representation of a cylinder above the representation of the patient 214 (FIGS. 6-9) and the surgical site 1270 (FIGS. 6-9).

With reference again to FIGS. 1 and 2, initial surgical incisions are generally similar in size and shape for each particular orthopedic surgical procedure. Using a standard sized incision as a reference along with approximations of where the boundary should be visualized based on surgeon input, an unoptimized starting boundary may be provided. Initial placement of the tracked marker 215 may be a specific placement relative to the incision. Thus, the incision and initial unoptimized boundary conditions may be, for example, displayed as a representation of a colored cylinder (FIG. 6) distinct from other objects, with clear warnings that the boundary is not optimized. The default boundary 225 of the no-go-zone 212, may be determined, for example, by a combination of the initial position of the surgical robot 200, the bone position 110 (FIG. 10), dynamic obstacle positions 111 (FIG. 10), and the static cut path 106 (FIG. 10). The default boundary 225 may have a default go-zone 216.

Since human joints generally have two interfacing members, the default go-zone 216 may be, for example, created based on the two interfacing joint members. For example, the hip (e.g., acetabular cup+femoral component), knee (e.g., femur+tibia) may result in a go-zone 216. Generally, the default go-zones or free zones may be created so the go-zone could be the permissible movement area of the no-go-zone for each member. The representation of the patient 1214 may be moved, and the simulation adjusted so that the surgical site 1270 and simulation spatially overlap on visual display screen 400. It is at this point that the cut path execution data 119 (FIG. 10) may need to be refined, with, for example, the registration process 113 (FIG. 10) performed to update the bone position 110 (FIG. 10) and dynamic obstacles positions 111 (FIG. 10), and the static cut path 106 (FIG. 10) updated. Updates to static cut path may include, for example determine a more suitable angle and an updated orientation for cutting tool 203 (FIG. 10). Default no-go-zone 212 may also be updated at this time.

During no-go-zone training 104 (FIG. 10), the surgical robot 200 may be placed in zero-g mode and moved by the control handle 201 to a safe position, as determined by a surgeon, within the default boundary 225 defining the no-go-zone 212. A second go-zone 1311 (FIG. 7) may be expanded, for example, in a conical motion using a position lock to create an enlarged go-zone 1312 (FIG. 8). The cutting tool 203 and the end effector 202 may be the parts of the surgical robot 200 which would be placed within the no-go-zone 212 to define go-zones. Using the control handle 201 to move the surgical robot 200, the act of creating go-zones 216 within a no-go-zone 212 may be performed by, for example, positioning the cutting tool 203 within a no-go-zone and pressing a record button 331 (FIG. 6) on the visual display screen 400 (FIG. 6) to record the position of the cutting tool 203 or end effector 202. The recorded position may become go-zones 216, overriding previously defined no-go-zones 212. Go-zones 216 may be in the shape of the cutting tool 203 or the end effector 202 or a combination of the two. The step of recording individual go-zone positions may be repeated, creating multiple go-zones 216 (only one of which is shown in FIGS. 1 and 2). Default go-zone 310 being in close linear proximity to a second go-zone 1311 (FIG. 7) may be automatically merged to include space between a default go-zone 310 and a second go-zone 1311 (FIG. 7). Individual go-zones 216 may be merged by selection of the union function 332 (FIG. 7) on the visual display screen 400 (FIG. 7).

When a final go-zone 1312 (FIG. 7) has been created, refined no-go-zone data 105 (FIG. 10) may be sent to the cut path execution block 107 (FIG. 10). At this point, the cut path might be updated or the positioning and movements of the surgical robot 200 to perform the cut may be updated. The refined no-go-zone data 105 (FIG. 10) will reflect a no-go-zone 212 with a final go-zone 1313 (FIG. 7). The go-zones 216 and no-go-zone 212 may be communicated to the robot 200 because the position and orientation of the zones was mapped using the known positions of the end effector 202 and the cutting tool 203. Furthermore, the position of the go-zones 216 and the no-go-zone 212 relative to the surgical site 270 may also be determined to the robot 200 as a result of the bone position 110 (FIG. 10) and the dynamic obstacle positions 111 (FIG. 10) being determined. Robot commands 108 (FIG. 10) may be sent to the surgical robot 200 by the cut path execution block 107 (FIG. 10). The robot commands 108 (FIG. 10) may include, for example the refined no-go-zone data 105 (FIG. 10), the static cut path 106 (FIG. 10), the bone position 110 (FIG. 10), and the dynamic obstacle positions 111 (FIG. 10). The boundaries may be displayed on the visual display screen 400 (FIG. 7) and the boundaries may be adjusted through touch interaction with the screen 400 (FIG. 7), or the use of a mouse, or by moving the surgical robot 200 using surgical handle 201.

As used here, the term inter-operative means that the method of FIG. 10 may be conducted at a point during the surgical operation, and usually once the target bone is exposed. While steps are performed prior to entering the surgical theater, the described methods may be used during surgery and the cutting path may be adjusted to accommodate changes which may arise during surgery.

During mapping, it may be possible to define never-go-zones in the system, which can be created to prevent any form of override. The never-go-zones may be created by, for example, using the mouse or the touch screen features of the visual display screen 400 (FIGS. 6-9) to select areas of the visually displayed boundary.

Prior to the cut mode being initiated, the surgical robot 200 must be moved into proximity of a cut start point. Once the cut mode is initiated by an appropriate control button, the surgical robot 200 may perform a confirmation check to determine whether the correct cutting tool 203 is connected to the end effector 202. Also, the surgical robot will check if the cutting tool 203 selected can complete the programmed cut from the selected starting point. The surgical robot 200 may then be used to perform a surgical cut as defined by robot commands 108 (FIG. 10). The performance of the robot commands 108 (FIG. 10) to complete a surgical cut or a series of surgical cuts may be known as a surgical protocol.

During surgery, retractors are used to move soft tissue out of the trajectory of a cutting tool and to provide clear access to a bone. It is common for soft tissue to move during the cut and the surgical protocol may need to be updated to accommodate such changes. In one embodiment, a registration process 113 (FIG. 10) and the camera tracker 112 (FIG. 10) may dynamically update bone position and dynamic obstacle positions while a surgical cut is performed. If tissue moves but is within a no-go-zone, the surgical robot 200 may proceed with the cut.

As part of the registration process 113 (FIG. 10), the retractors used during surgery may be identified and used to define the default no-go-zone 310. Once the registration process 113 (FIG. 10) and the boundaries are defined, the surgical robot 200 may be able to operate dynamically by performing a chaining operation to transform the positions of the boundaries relative to a frame of reference defined by the base 211 (e.g., world frame of reference). With the boundaries defined in relation to the world frame, along with other positions, moving retractors or boundaries may continue to be recalculated and updated as the surgical robot proceeds through the cut.

Figure 11:
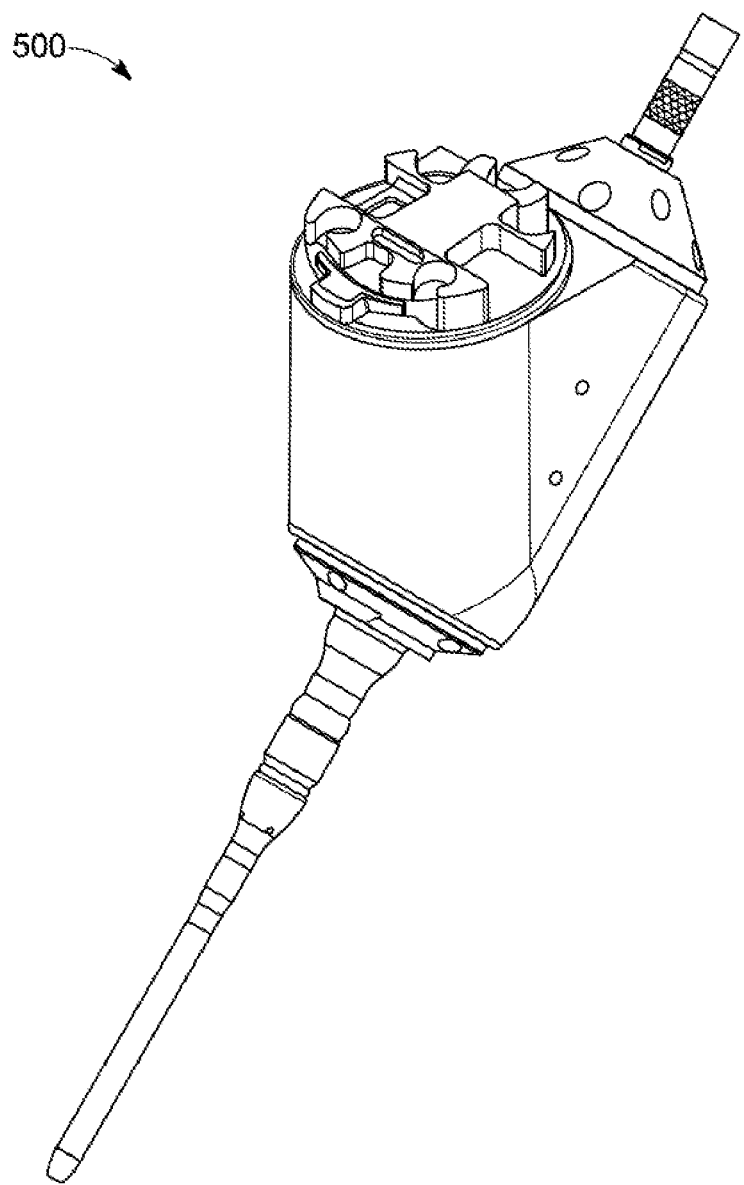
FIG. 11 is a perspective view of an end effector and tool, according to an embodiment of the present disclosure.
Figure 12:
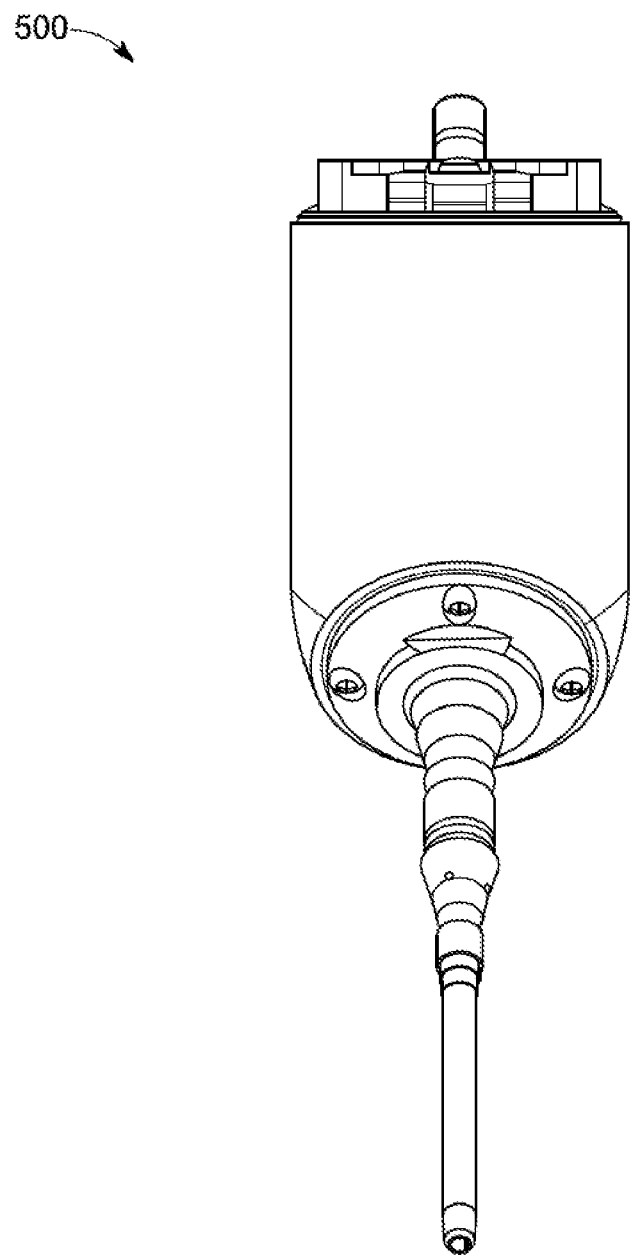
FIG. 12 is a front elevational view of the end effector and tool of FIG. 11, according to an embodiment of the present disclosure.
Figure 13:
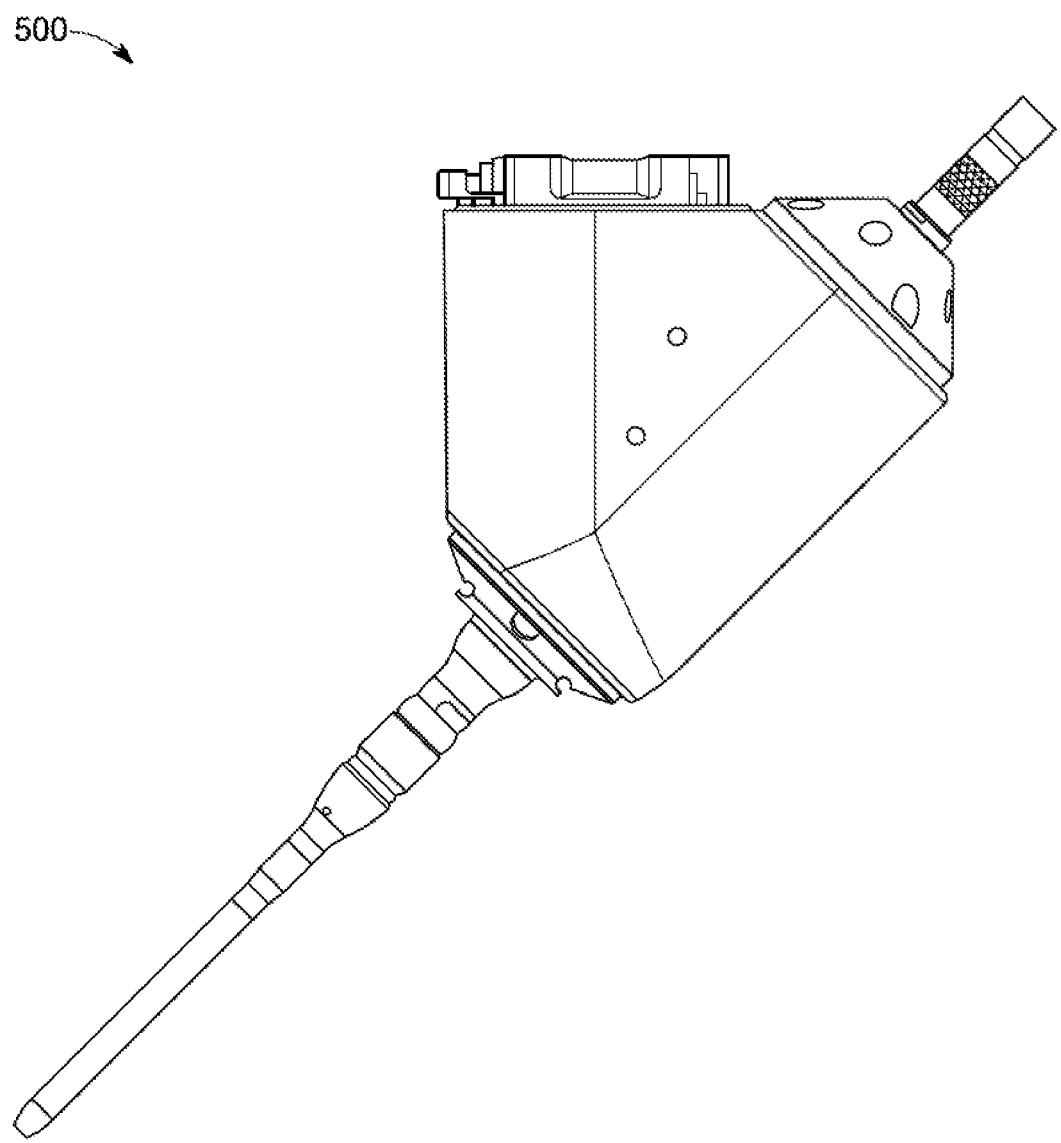
FIG. 13 is a side elevational view of the end effector and tool of FIG. 11, according to an embodiment of the present disclosure.

FIGS. 11-13 illustrate an end effector 500 being ergonomically configured, according to an embodiment of the present disclosure. For example, a separate handle or control handle need not be provided, but the end effector may be shaped to be grabbed by the user or surgeon. On or more buttons may be provided on the end effector 500, similar to the buttons described above. For example, various mode switch buttons may be provided on the side or the rear of the end effector and may be pressed by any finger of the user. In some embodiments, the mode switch buttons may toggle between a zero-gravity mode and an active milling mode. In the zero-gravity mode, the user or surgeon may be able to move the robot unconstrained. In some embodiments, the mode switch buttons may be designed to be depressed once and not continuously. In other embodiments, the control buttons may be provided elsewhere such as foot pedals disposed on the floor.

Figure 14:
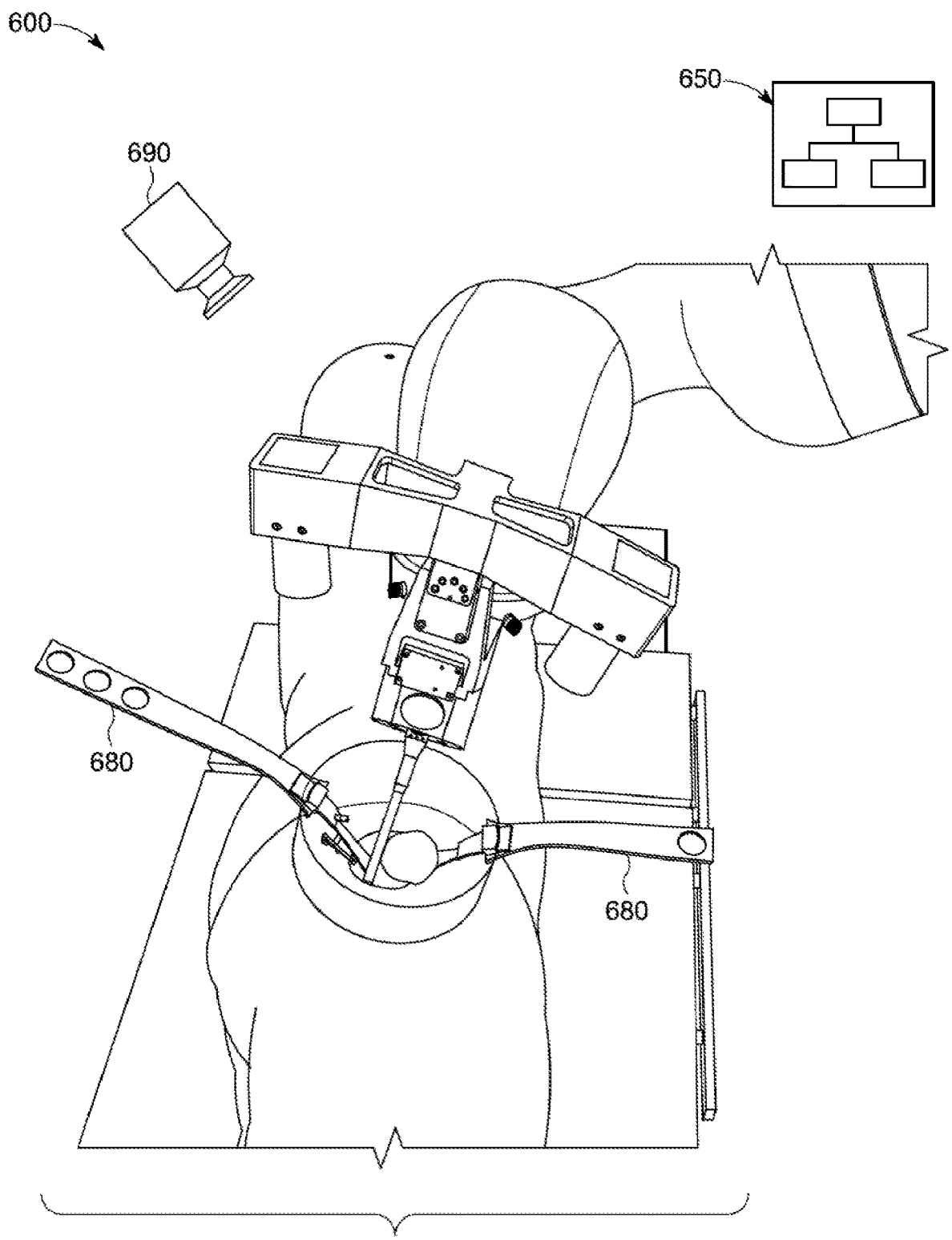
FIG. 14 is a perspective top view of a surgical site and end effector of a surgical robot as observed by a secondary camera, according to an embodiment of the present disclosure.

FIG. 14 illustrates a surgical robotic system 610 having a surgical robot 600, a control unit 650, and a secondary camera 690, according to an embodiment of the present disclosure. For example, the secondary camera 690 may be operable to track one or more retractors 680. The secondary cameral 690 may be a secondary camera that is not used to track the position of the surgical robot arm. The secondary camera 690 may be mounted to the arm or is stationary on a cart, or elsewhere in the operating room.

FIG. 15 illustrates a surgical method 700, according to an embodiment of the present disclosure. In this illustrated embodiment, the robotic surgical method 700 may include at 710 positioning a patient relative to a robot, at 720 moving an end effector of the robot relative to a surgical site of a patient, at 730 defining a go-zone and a no-go-zone associated with the surgical site based on the moving the end effector of the robot relative to the patient, and at 740 effecting a surgical procedure at the surgical site of the patient with a tool attached to the end effector of the robot based on the defined go-zone and the defined no-go-zone and wherein the effecting the surgical procedure maintains the tool in the defined go-zone and avoids contact with the defined no-go-zone.

Figure 16:
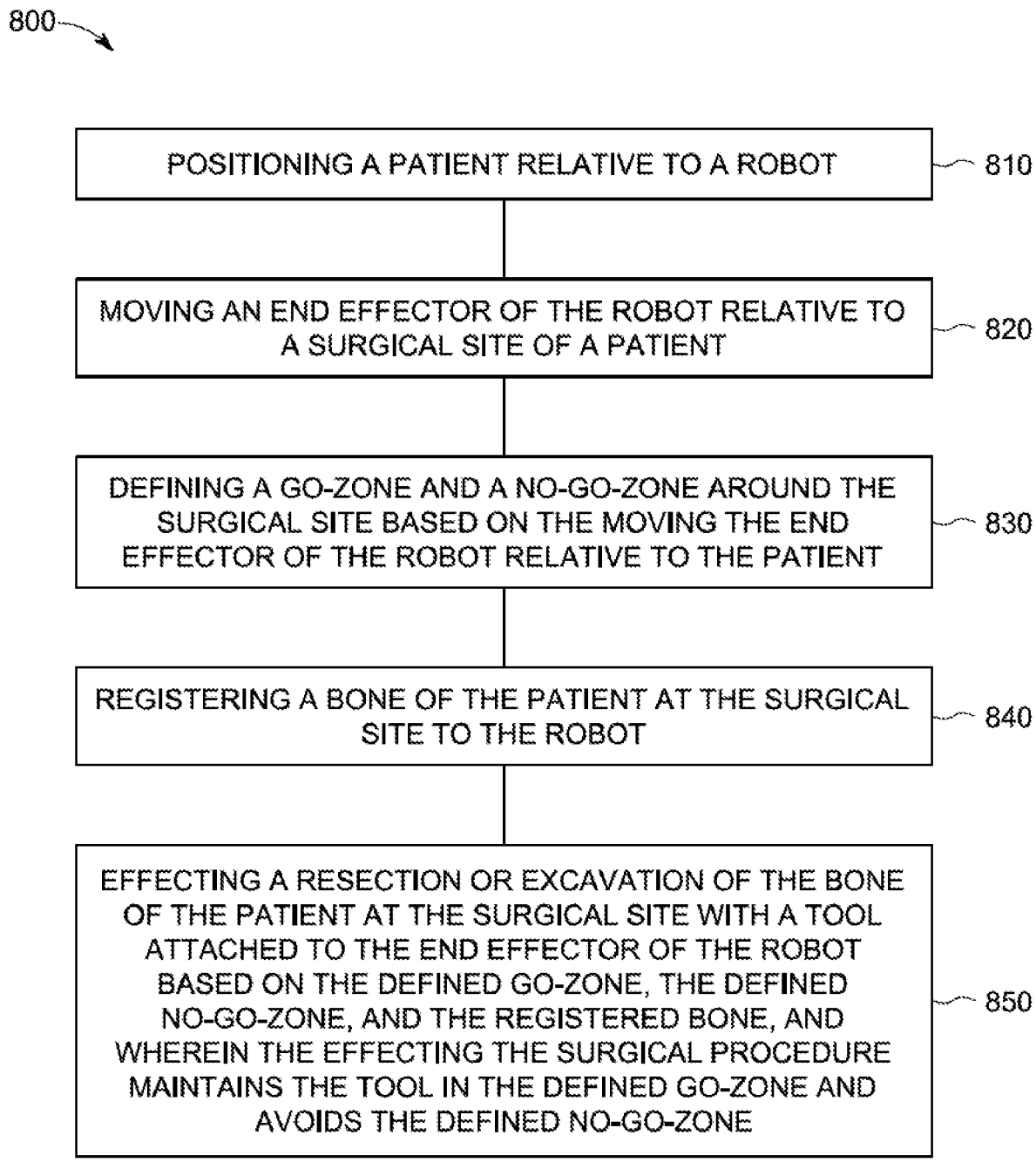
FIG. 16 is a flowchart of a surgical method, according to an embodiment of the present disclosure.

FIG. 16 illustrates a surgical method 800, according to an embodiment of the present disclosure. In this illustrated embodiment, the robotic surgical method 800 may include, at 810 positioning a patient relative to a robot, at 820 moving an end effector of the robot relative to a surgical site of a patient, at 830 defining a go-zone and a no-go-zone around the surgical site based on the moving the end effector of the robot relative to the patient, at 840 registering a bone of the patient at the surgical site to the robot, and at 850 effecting a resection or excavation of the bone of the patient at the surgical site with a tool attached to the end effector of the robot based on the defined go-zone, the defined no-go-zone, and the registered bone, and wherein the effecting the surgical procedure maintains the tool in the defined go-zone and avoids the defined no-go-zone.

Figure 17:
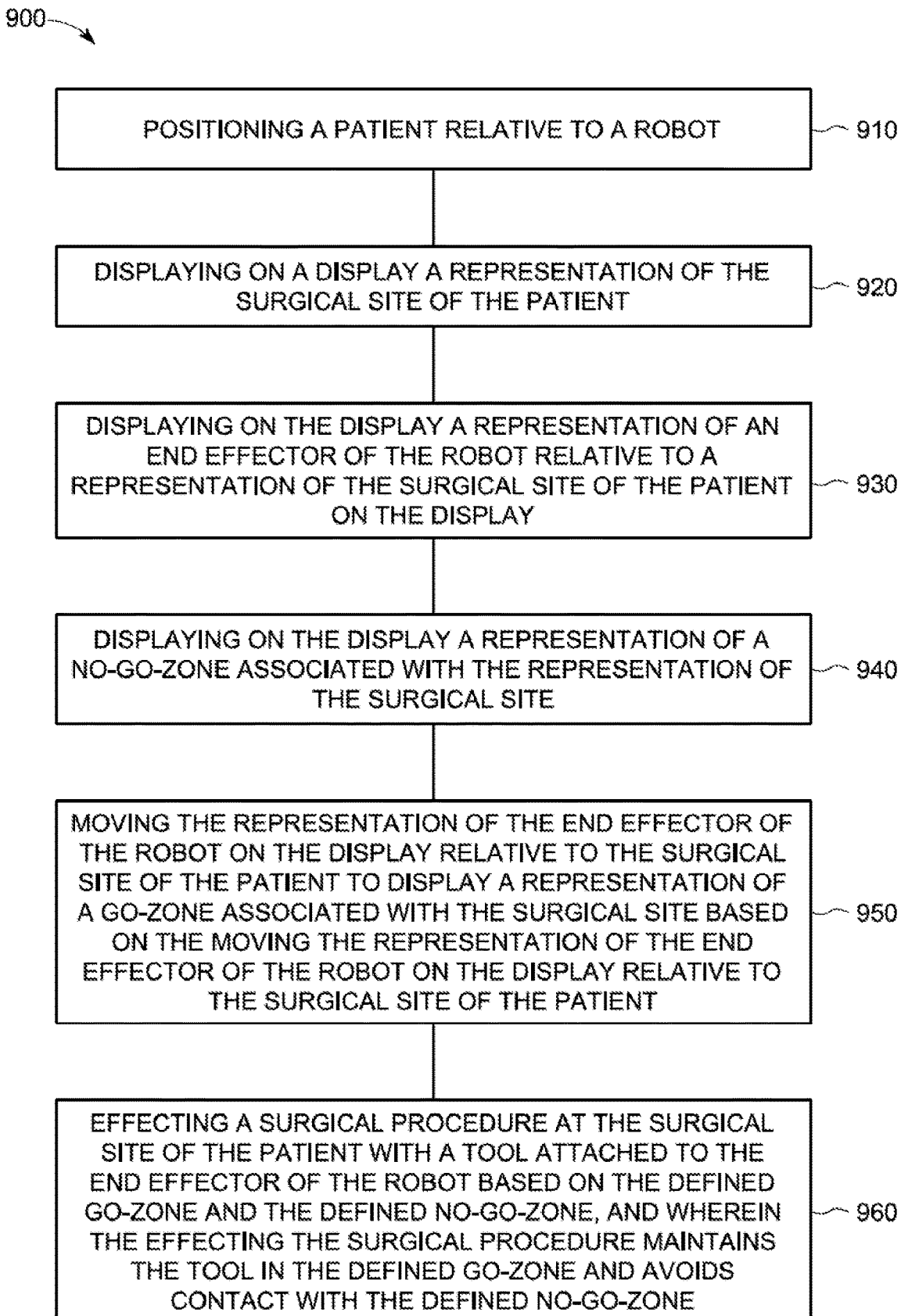
FIG. 17 is a flowchart of a surgical method, according to an embodiment of the present disclosure.

FIG. 17 illustrates a surgical method 900, according to an embodiment of the present disclosure. In this illustrated embodiment, the robotic surgical method 900 may include, at 910 positioning a patient relative to a robot, at 920 displaying on a display a representation of the surgical site of the patient, at 930 displaying on the display a representation of an end effector of the robot relative to a representation of the surgical site of the patient on the display, at 940 displaying on the display a representation of a no-go-zone associated with the representation of the surgical site, at 950 moving the representation of the end effector of the robot on the display relative to the surgical site of the patient to display a representation of a go-zone associated with the surgical site based on the moving the representation of the end effector of the robot on the display relative to the surgical site of the patient, at 960 effecting a surgical procedure at the surgical site of the patient with a tool attached to the end effector of the robot based on the defined go-zone and the defined no-go-zone, and wherein the effecting the surgical procedure maintains the tool in the defined go-zone and avoids contact with the defined no-go-zone.

Figure 18:
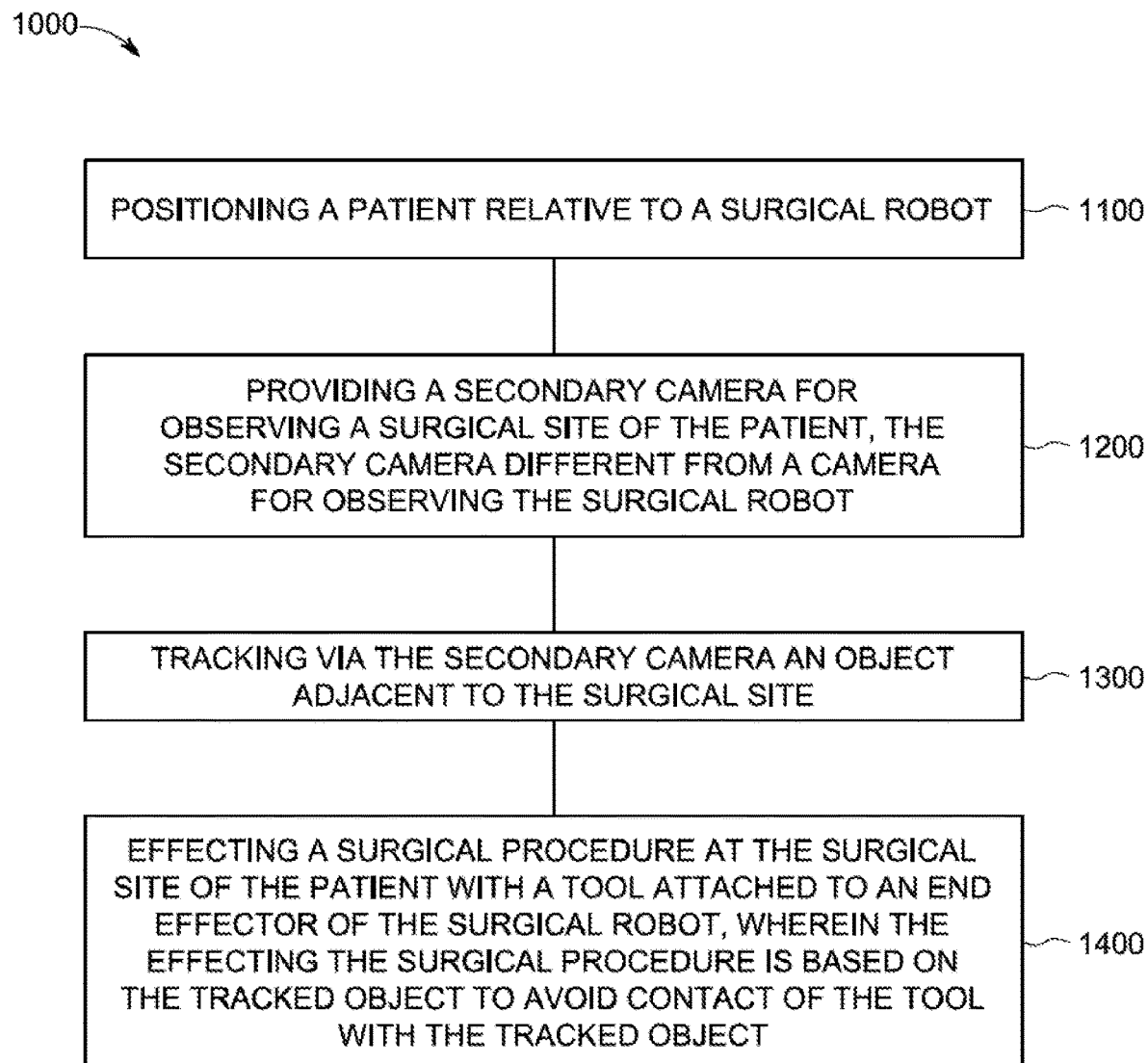
FIG. 18 is a block diagram of a system, according to an embodiment of the present disclosure.

FIG. 18 illustrates a surgical method 1000, according to an embodiment of the present disclosure. In this illustrated embodiment, an object such as at least one retractor is tracked for avoidance during a surgical procedure. For example, the robotic surgical method 1000 may include, at

1100 positioning a patient relative to a surgical robot, at 1200 providing a secondary camera having for observing a surgical site of the patient, the secondary camera different from a camera for observing the surgical robot, at 1300 tracking via the secondary camera an object adjacent to the surgical site, and at 1400 effecting a surgical procedure at the surgical site of the patient with a tool attached to an end effector of the surgical robot, and wherein the effecting the surgical procedure is based on the tracked object to avoid contact of the tool with the tracked object.

In some embodiments, the robotic surgical method may include the secondary camera being disposed on the surgical robot for observing the surgical site, the secondary camera includes a field of view limited to observing the surgical site, the effecting the surgical procedure being based on a cut plan, the effecting the surgical procedure is based on a cut plan modified based on the tracked object, the effecting the surgical procedure is based on a go zone and a no-go zone, the effecting includes automatically effecting the surgical procedure, the object is at least one retractor, the tracking includes tracking via the secondary camera a marker attached to the object, and/or the object includes bone, muscles, ligaments, and/or tissue.

Figure 19:
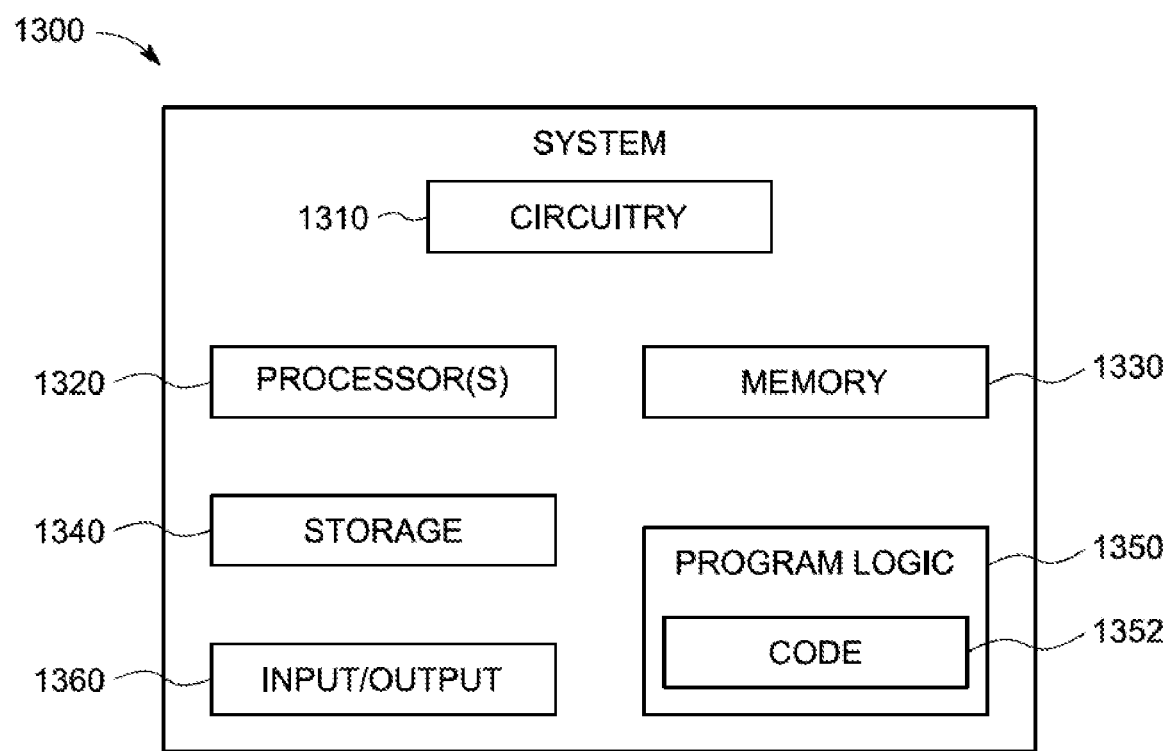
FIG. 19 is a block diagram of a control unit operable for use in the surgical robotic system such as surgical robotic system, according to an embodiment of the present disclosure.

FIG. 19 illustrates a block diagram of a control unit 1300 operable for use in the surgical robotic system such as surgical robotic system 10 (FIG. 1), according to an embodiment of the present disclosure. System 1300 may include a circuitry 1310 that may in certain embodiments include a microprocessor 1320. The system 1300 may also include a memory 1330 (e.g., a volatile memory device), and storage 1340. The system 1300 may include a program logic 1350 including code 1352 that may be loaded into or stored in the memory 1330, the storage 1340, and/or circuitry 1310, and executed by the microprocessor 1320 and/or circuitry 1310. The various components may be operably coupled directly or indirectly via a system bus or may be coupled directly or indirectly to other data processing systems and components. The program logic 1350 may include the program code discussed above in this disclosure for use in forming or resecting a patient's proximal portion of a femur.

As will be appreciated by one skilled in the art, aspects of the technique may be embodied as a system, method, or computer program product. Accordingly, aspects of the technique may take the form of an entirely hardware embodiment, an entirely software embodiment (including firmware, resident software, micro-code, etc.) or an embodiment combining software and hardware aspects that may all generally be referred to herein as a "circuit," "module" or "system."

It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. Each block in the flowchart or block diagrams may represent a module, segment, or portion of code, which includes one or more executable instructions for implementing the specified logical function(s).

These computer program instructions, also referred to as software and/or program code, may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. For example, in a particular arrangement, a desktop or workstation computer may be employed using a commercially available operating system, e.g., Windows®, OSX®, UNIX or Linux based implementation.

As shown in FIG. 19, the computer readable storage medium 1340 may be, for example, but not limited to, an electronic, magnetic, optical, electromagnetic, infrared or semiconductor system, apparatus, or device, or any suitable combination of the foregoing. The storage 1340 may include an internal storage device, an attached storage device and/or a network accessible storage device. More specific examples (a non-exhaustive list) of the computer readable storage medium include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

Computer program code for carrying out operations for aspects of the present technique may be written in any combination of one or more programming languages, including an object oriented programming language, such as Java, Smalltalk, C++ or the like, and conventional procedural programming languages, such as the "C" programming language, PHP, ASP, assembler or similar programming languages, as well as functional programming languages and languages for technical computing. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). Furthermore, more than one computer can be used for implementing the program code, including, but not limited to, one or more resources in a cloud computing environment.

As shown in FIG. 19, Input/output or I/O devices 1360 (including, but not limited to, keyboards, displays, pointing devices, DASD, tape, CDs, DVDs, thumb drives and other memory media, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the available types of network adapters.

Data relating to a patient, e.g., the patient's hip and pelvis, may be created by, or accessed from, a medical sensor device. For example, previous medical scans of an extremity, such as those obtained from a computerized axial tomography (CAT or CT) or magnetic resonance imaging (MRI) scan may be stored in a medical record storage apparatus, in storage 1340, or accessed by system 1300. Such patient data may include other data for a given patient (e.g., bone density, type, length, medical conditions etc.). By way of a non-limiting example, the patient data may include a scan data set containing a series of two-dimensional images obtained from the scanning device (e.g., CT scan slices). As such, the scan data set is a 3D dimensional representation of the scan data.

A1. A robotic surgical device includes a processor configured with executable code to transform surgical plan data into a surgical protocol, memory, a storage medium having a database, a user interaction system, a plurality of joints, a plurality of body parts, a base, a flange, and a marker. The base has a longitudinal axis, the plurality of joints includes a first joint, a second joint, a third joint, a fourth joint, a fifth joint, and a sixth joint. Each joint has a first end and a second end. The plurality of body parts includes a first body part, a second body part, a third body part, a fourth body part, a fifth body part, and a sixth body part. Each body part has a first end and a second end. The sixth joint is rotatably connected to the base and movable about the longitudinal axis at the sixth joint first end; the sixth joint is further rotatably connected to the sixth body part at the sixth body part first end, with the sixth body part being rotatably movable relative to the base at the sixth joint second end. The fifth joint is rotatably connected at the fifth joint first end to the sixth body part second end and rotatably connected at the fifth joint second end to the fifth body part first end. The fifth body part and the sixth body part are rotatably movable relative to each other. The fourth joint is rotatably connected at the fourth joint first end to the fifth body part second end and rotatably connected at the fourth joint second end to the fourth body part first end. The fourth body part and the fifth body part are rotatably movable relative to each other. The third joint is rotatably connected at the third joint first end to the fourth body part second end and rotatably connected at the third joint second end to the third body part first end. The third body part and the fourth body part are rotatably movable relative to each other. The second joint is rotatably connected at the second joint first end to the third body part second end and rotatably connected at the second joint second end to the second body part first end. The second body part and the third body part are rotatably movable relative to each other. The first joint is rotatably connected at the first joint first end to the second body part second end and rotatably connected at the first joint second end to the first body part first end. The first body part and the second body part are rotatably movable relative to each other. The first body part second end being rotatably connected to the flange. The flange being rotatable relative to the first body part. The user interaction system includes at least one camera, a control handle, and a visual display, with the at least one camera and the control handles connected to the flange.

A2. The robotic surgical device of A1, wherein the control handle further includes a primary thumb button, a secondary thumb button, a trigger button, and a position switch. A3. The robotic surgical device as in A1 or A2, wherein the marker is located at a surgical site, the marker being usable for determining the position of an object relative to the base. A4. The robotic surgical device as in any of A1-A3, wherein the user interaction system being usable for data exchange.

B1. A method for performing surgery using a robotic surgical device, the method steps includes: providing the robotic surgical device having a processing circuit configured to transform surgical plan data into a surgical protocol, memory, a storage medium having a database, a user interaction system, a plurality of joints, a plurality of body parts, a base, a flange, a relative position marker, a camera, an end effector, and a cutting tool; wherein the user interaction system includes a control handle, the camera, and a visual display device; gathering surgical plan data to create a default boundary constraint; modifying the default boundary constraint inter-operatively using the user interaction system to create modified surgical plan data; providing a cut path; creating the surgical protocol; and performing at least one cut in accordance to the surgical protocol by the robotic surgical device.

B2. The method of B1, wherein the gathering of the surgical plan data includes, inter-operatively gathering positional measurements including: using the camera, the relative position marker, and a bone marker on a bone of a patient to gather relative positions for the robotic surgical device, and calculating the relative position data by the robotic surgical device. B3. The method of B2, wherein the gathering of the surgical plan data further includes, the processor using relative position data to define at least one default go-zone and at least one default no-go-zone; wherein the default boundary constraint includes the at least one default go-zone and at least default one no-go-zone. B4. The method as in B1 or B2, wherein the gathering of the surgical plan data further includes, the processor using relative position data to define at least one default go-zone and at least one default no-go-zone; wherein the default boundary constraint includes the at least one default go-zone and at least default one no-go-zone. B5. The method of B3, wherein defining a default no-go-zone includes identifying a retractor within a field of view of the camera. B6. The method as in any of B1, B2, B3, wherein defining a default no-go-zone includes identifying a retractor within a field of view of the camera. B7. The method of B5, wherein identifying the retractor within a field of view of the camera is continuously performed and added to a new no-go-zone. B8. The method as in B1, B2, B3, B5, or B7, wherein modifying the default boundary constraint inter-operatively through the user interaction system includes repeating moving the robotic surgical device using the control handle into a plurality of positions within the default boundary constraint and defining each position as a no-go position until a plurality of safe positions and a plurality of no-go positions are defined; and performing a union of the plurality of safe positions and a union of the plurality of no-go positions to create a new go-zone and the new no-go-zone. B9. The method of B8, wherein modifying the default boundary constraint inter-operatively through the user interaction system further includes, creating modified surgical plan data comprising the new go-zone and the new no-go-zone. B10. The method as in any of B1, B2, B3, B5, or B7, wherein creating the surgical protocol by the robotic surgical tool includes: providing a bone position and a dynamic obstacle position; and combining relative position data, the bone position, the dynamic obstacle position, modified surgical plan data, and a cut path to define the surgical protocol. B11. The method of B10, wherein creating the surgical protocol by the robotic surgical tool includes: providing a bone position and a dynamic obstacle position; and combining relative position data, the bone position, the dynamic obstacle position, modified surgical plan data, and a cut path to define the surgical protocol. B12. The method of B11, wherein creating the surgical protocol by the robotic surgical tool includes: providing a bone position and a dynamic obstacle position; and combining the relative position data, the bone position, the dynamic obstacle position, modified surgical plan data, and a cut path to define the surgical protocol.

C1. A robotic surgical method comprising: creating an incision to access a first bone; creating a surgical site; inserting and fastening a position bone marker to a second bone; positioning a robotic surgical device using a control handle; using a robotic surgical device camera to view the surgical site; using a pointer to point to a plurality of positions on the first bone; collecting bone position data on the plurality of positions on the first bone relative to the relative the position bone marker; processing and storing the bone position data relative to a base of the robotic surgical device; using the position bone marker to identify a plurality of obstacles within the surgical site; collecting dynamic obstacle position data within the surgical site relative to the position bone marker; processing and storing dynamic obstacle position data relative to the base of the robotic surgical device; providing a static cut path; viewing the static cut path, bone position data, and dynamic obstacle position data on a visual display; positioning the robotic surgical device using the control handle to a position near the surgical site to create a boundary constraint; moving the robotic surgical device using the control handles to safe positions; creating an updated boundary constraint; providing the boundary constraint data, the static cut path data, the bone position data, and the dynamic obstacle position data to create a surgical protocol data; and performing at least one cut using surgical protocol data.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The present disclosure has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the present disclosure be construed as including all such modifications and alterations.

As may be recognized by those of ordinary skill in the art based on the teachings herein, numerous changes and modifications may be made to the above-described and other embodiments of the present disclosure without departing from the scope of the present disclosure. The projections, coupling segment, and other components of the device and/or system as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the devices and systems may include more or fewer components or features than the embodiments as described and illustrated herein. For example, the components and features of the present disclosure may all be used interchangeably and in alternative combinations as would be modified or altered by one of skill in the art. Accordingly, this detailed description of the currently-preferred embodiments is to be taken in an illustrative, as opposed to limiting of the present disclosure.

What is claimed is:

1. A robotic surgical method comprising:
   positioning a patient relative to a robot;
   moving an end effector of the robot relative to a surgical site of a patient;
   defining a go-zone and a no-go-zone associated with the surgical site based on the moving the end effector of the robot relative to the patient;
   effecting a surgical procedure at the surgical site of the patient with a tool attached to the end effector of the robot based on the defined go-zone and the defined no-go-zone; and
   wherein the effecting the surgical procedure maintains the tool in the defined go-zone and avoids contact with the defined no-go-zone; and
   the defining the go-zone and the no-go-zone comprises:
   defining the no-go-zone; and
   the moving the end effector to carve out one or more portions of the no-go-zone to define the go-zone.

2. The robotic surgical method of claim 1, wherein the effecting the surgical procedure is based on a cut plan, the defined go-zone, and the defined no-go-zone.

3. The robotic surgical method of claim 1, wherein the moving comprises moving the end effector of the robot along an arc, and the defining the go-zone is based on the moving the end effector of the robot relative to the patient along the arc.

4. The robotic surgical method of claim 1, wherein the moving comprises moving the end effector of the robot along an arc to define a portion of a cylinder or a cone, and the defining the go-zone is based on the moving the end effector of the robot relative to the patient along the arc defining the portion of the cylinder or the cone.

5. The robotic surgical method of claim 1, wherein the moving comprises:
   moving the end effector of the robot relative to the surgical site of the patient in a first path; and
   moving the end effector of the robot relative to the surgical site of the patient in a second path different from the first path; and wherein,
   the defining a go-zone comprises:
   defining the go-zone around the surgical site comprises a combined go-zone based on the moving the end effector of the robot relative to the patient along the first path and the second path.

6. The robotic surgical method of claim 1, wherein the moving comprises a user moving the end effector of the robot.

7. The robotic surgical method of claim 1, wherein the moving comprises:
receiving a user initiating input at a beginning of the moving of the end effector of the robot relative to the surgical site of the patient; and
receiving a user ending input at an end of the moving of the end effector of the robot relative to the surgical site of the patient.

8. The robotic surgical method of claim 1, wherein the moving comprises a user operably grasping the end effector of the robot.

9. The robotic surgical method of claim 1, wherein the moving comprises:
a user operably grasping the end effector of the robot;
receiving a user initiated input in response to a button pressed at a beginning of the moving of the end effector of the robot relative to the surgical site of the patient; and
receiving a user ending input in response to the release of the button press at an end of the moving of the end effector of the robot relative to the surgical site of the patient.

10. The robotic surgical method of claim 1, further comprising:
defining an object associated with the surgical site; and
wherein:
the effecting comprises effecting the surgical procedure based on the defined go-zone, the defined no-go-zone, and the defined object, and the effecting the surgical procedure maintains the tool in the defined go-zone and avoids contact in the defined no-go-zone and with the defined object.

11. The robotic surgical method of claim 10, wherein the object comprises a retractor.

12. The robotic surgical method of claim 10, wherein the defining the object comprises obtaining data of the object at the surgical site or data of a marker attached to the object at the surgical site.

13. The robotic surgical method of claim 12, wherein the obtaining data of the object at the surgical site or data of a marker attached to the object at the surgical site comprises obtaining video data within a field of view of a camera attached to the robot or obtaining video data within a field of view of using a secondary camera directed toward the surgical site.

14. The robotic surgical method of claim 13, wherein the defining the object comprises continuously defining the object at the surgical site, and the effecting comprises effecting the surgical procedure based on the defined go-zone, the defined no-go-zone, and the continuously defined object, and the effecting the surgical procedure maintains the tool in the defined go-zone and avoids contact in the defined no-go-zone and with the defined object.

15. The robotic surgical method of claim 1, wherein the effecting further comprises effecting the surgical procedure to avoid contact of the surgical robot parts and/or robot joints with the defined no-go-zone.

16. A robotic surgical method comprising:
positioning a patient relative to a robot;
moving an end effector of the robot relative to a surgical site of a patient;
defining a go-zone and a no-go-zone around the surgical site based on the moving the end effector of the robot relative to the patient;
registering a bone of the patient at the surgical site to the robot;
effecting a resection or excavation of the bone of the patient at the surgical site with a tool attached to the end effector of the robot based on the defined go-zone, the defined no-go-zone, and the registered bone; and
wherein the effecting the surgical procedure maintains the tool in the defined go-zone and avoids the defined no-go-zone; and
the defining the go-zone and the no-go-zone comprises:
defining the no-go-zone; and
the moving the end effector to carve out one or more portions of the no-go-zone to define the go-zone.

17. The robotic surgical method of claim 16, wherein the registering the bone comprises:
obtaining data of the bone at the surgical site or data of a marker attached to the bone at the surgical site.

18. The robotic surgical method of claim 17, wherein the obtaining data of the bone at the surgical site or data of a marker attached to the bone at the surgical site comprises obtaining video data within a field of view of a secondary camera directed toward the surgical site.

19. A robotic surgical method comprising:
positioning a patient relative to a robot;
displaying on a display a representation of the surgical site of the patient;
defining on the display a no-go-zone and a go-zone associated with the representation of the surgical site;
effecting a surgical procedure at the surgical site of the patient with a tool attached to an end effector of the robot based on the defined go-zone and the defined no-go-zone; and
wherein the effecting the surgical procedure maintains the tool in the defined go-zone and avoids contact with the defined no-go-zone; and
the defining on the display the go-zone and the no-go-zone comprises: defining the no-go-zone; and
the moving the end effector to carve out one or more portions of the no-go-zone to define the go-zone.

20. The robotic surgical method of claim 19, wherein the defining comprises:
displaying on the display a representation of the end effector of the robot relative to the representation of the surgical site of the patient on the display; displaying on the display a representation of the no-go-zone associated with the representation of the surgical site; and
the moving the end effector comprises moving the representation of the end effector of the robot on the display relative to the surgical site of the patient to carve out one or more portions of the representation of the no-go-zone to define the go-zone.

21. A surgical system comprising:
a robot comprising a movable arm having an end effector;
a controller comprising a memory, one or more processors in communication with the memory, and program instructions executable by the one or more processors via the memory to perform a method, the method comprising:
receiving data associated with moving the end effector of the robot relative to the surgical site of a patient;
defining a go-zone and a no-go-zone associated with the surgical site based on the moving the end effector of the robot relative to the patient;
effecting a surgical procedure at the surgical site of the patient with a tool attached to the end effector of the robot based on the defined go-zone and the defined no-go-zone; and wherein the effecting the surgical procedure maintains the tool in the defined go-zone and avoids contact with the defined no-go-zone; and the defining the go-zone and the no-go-zone comprises:
defining the no-go-zone; and
the moving the end effector to carve out one or more portions of the no-go-zone to define the go-zone.

22. A surgical system comprising:
a robot comprising a movable arm having an end effector;
a controller operably connected to the robot, the controller comprising a memory, one or more processors in communication with the memory, and program instructions executable by the one or more processors via the memory to perform a method, the method comprising:
receiving data corresponding to moving the end effector of the robot relative to a surgical site of a patient;
defining a go-zone and a no-go-zone around the surgical site based on the received data corresponding to moving the end effector of the robot relative to the patient;
registering a bone of the patient at the surgical site to the robot;
effecting a resection or excavation of the bone of the patient at the surgical site with a tool attached to the end effector of the robot based on the defined go-zone, the defined no-go-zone, and the registered bone; and
wherein the effecting the surgical procedure maintains the tool in the defined go-zone and avoids the defined no-go-zone; and
the defining the go-zone and the no-go-zone comprises:
defining the no-go-zone; and
the moving the end effector to carve out one or more portions of the no-go-zone to define the go-zone.

23. A surgical system comprising:
a robot comprising a movable arm having an end effector;
a controller comprising a memory, one or more processors in communication with the memory, and program instructions executable by the one or more processors via the memory to perform a method, the method comprising:
displaying on a display a representation of the surgical site of the patient:
displaying on the display a representation of an end effector of the robot relative to a representation of the surgical site of the patient on the display;
displaying on the display of a representation of a no-go-zone associated with the representation of the surgical site;
moving the representation of the end effector of the robot on the display relative to the surgical site of the patient to display a representation of a go-zone associated with the surgical site based on the moving the representation of the end effector of the robot on the display relative to the surgical site of the patient;
effecting a surgical procedure at the surgical site of the patient with a tool attached to the end effector of the robot based on the defined go-zone and the defined no-go-zone; and
wherein the effecting the surgical procedure maintains the tool in the defined go-zone and avoids contact with the defined no-go-zone; and
the moving comprises carving out one or more portions of the no-go-zone to define the go-zone.

24. A robotic surgical method comprising:
positioning a patient relative to a surgical robot;
providing a secondary camera having for observing a surgical site of the patient, the secondary camera different from a camera for observing the surgical robot;
tracking via the secondary camera an object adjacent to the surgical site;
effecting a surgical procedure at the surgical site of the patient with a tool attached to an end effector of the surgical robot; and
wherein the effecting the surgical procedure is based on a defined no-go-zone, a moving the end effector to carve out one or more portions of the no-go-zone to define a go-zone, and the tracked object to avoid contact of the tool with the tracked object.

25. The robotic surgical method of claim 24, wherein the secondary camera is disposed on the surgical robot for observing the surgical site.

26. The robotic surgical method of claim 24, wherein the secondary camera comprises a field of view limited to observing the surgical site.

27. The robotic surgical method of claim 24, wherein the effecting the surgical procedure is based on a cut plan.

28. The robotic surgical method of claim 27, wherein the effecting the surgical procedure is based on a cut plan modified based on the tracked object.

29. The robotic surgical method of claim 24, wherein the effecting comprises automatically effecting the surgical procedure.

30. The robotic surgical method of claim 24, wherein the object is at least one retractor.

31. The robotic surgical method of claim 24, wherein the tracking comprises tracking via the secondary camera a marker attached to the object.

32. The robotic surgical method of claim 24, wherein the object comprises bone, muscles, ligaments, and/or tissue.

* * * * *